United States Patent
Chen et al.

(10) Patent No.: US 10,112,945 B2
(45) Date of Patent: Oct. 30, 2018

(54) FUSED QUINOLINE COMPUNDS AS PI3K, MTOR INHIBITORS

(71) Applicant: ADVENCHEN PHARMACEUTICALS, NANJING LTD., Jiangsu (CN)

(72) Inventors: Guoqing Paul Chen, Moorpark, CA (US); Changren Yan, Moorpark, CA (US); Michael Reale, Moorpark, CA (US); Monica Chen, Moorpark, CA (US)

( * ) Notice: Subject to any disclaimer, the term of this patent is extended or adjusted under 35 U.S.C. 154(b) by 0 days.

(21) Appl. No.: 15/325,593

(22) PCT Filed: Jul. 11, 2015

(86) PCT No.: PCT/US2015/040076
§ 371 (c)(1),
(2) Date: Jan. 11, 2017

(87) PCT Pub. No.: WO2016/010869
PCT Pub. Date: Jan. 21, 2016

(65) Prior Publication Data
US 2017/0174687 A1    Jun. 22, 2017

Related U.S. Application Data

(60) Provisional application No. 62/024,192, filed on Jul. 14, 2014.

(51) Int. Cl.
*C07D 471/22* (2006.01)

(52) U.S. Cl.
CPC .................. *C07D 471/22* (2013.01)

(58) Field of Classification Search
CPC .................................................. C07D 471/22
See application file for complete search history.

(56) References Cited

U.S. PATENT DOCUMENTS

| | | | |
|---|---|---|---|
| 7,667,039 B2* | 2/2010 | Garcia-Echeverria | ........................ C07D 471/04 544/295 |
| 2010/0105696 A1* | 4/2010 | Garcia-Echeverria | ........................ A61K 31/4745 514/253.03 |
| 2016/0326138 A1 | 11/2016 | Chen et al. | |
| 2017/0182027 A1 | 6/2017 | Wang | |
| 2017/0202828 A1 | 7/2017 | Zhang | |

FOREIGN PATENT DOCUMENTS

| | | |
|---|---|---|
| CN | 101809012 | 8/2010 |
| CN | 102344438 | 2/2012 |
| WO | WO 2006/122806 | 11/2006 |
| WO | WO 2008/112407 | 9/2008 |
| WO | WO 2008/112408 | 9/2008 |
| WO | WO 2009/155527 | 12/2009 |
| WO | WO 2010/105761 | 9/2010 |
| WO | WO 2014/113616 | 7/2014 |

OTHER PUBLICATIONS

Bello, E. et al., E-3810 Is a Potent Dual Inhibitor of VEGFR and FGFR thatExerts Antitumor Activity in Multiple Preclinical Models, Cancer Research; 71(4), Feb. 15, 2011.
Moreno et al., Clin Transl Oncol (2010) 12:468-472.
Sala, F. et al., Development and validation of a high-performance liquid chromatography—tandem mass spectrometry method for the determination of the novel inhibitor of angiogenesis E-3810 in human plasma and its application in a clinical pharmacokinetic study, Journal of Mass Spectrometry, 2011, 46, pp. 1039-45.
Zhou, Y. et al., AL3810, a multi-tyrosine kinase inhibitor, exhibits potent anti-angiogenic and ant-tumor activity via targeting VEGFR, FGFR, and PDGFR, Journal of Cellular and Molecular Medicine, vol. 16, No. 10, 2012 pp. 2321-2330.
Traina et al.—Optimizing Chemotherapy Dose and Schedule by Norton-Simon Mathematical Modeling, Breast Dis (2010), vol. 31(1), pp. 1-21.

* cited by examiner

*Primary Examiner* — David K O'Dell
(74) *Attorney, Agent, or Firm* — Knobbe, Martens, Olson & Bear, LLP

(57) ABSTRACT

The present invention relates to the compounds of formula I, processes for their preparation, pharmaceutical compositions containing them as active ingredient, methods for the treatment of disease states associated with cancers associated with protein kinases, to their use as medicaments for use in the production of inhibition of mTor, pi3k reducing effects in warm-blooded animals such as humans.

Formula I

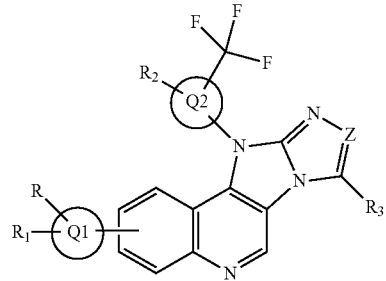

16 Claims, No Drawings

FUSED QUINOLINE COMPUNDS AS PI3K, MTOR INHIBITORS

INCORPORATION BY REFERENCE TO ANY PRIORITY APPLICATIONS

This application is the U.S. National Phase of International Application PCT/US15/40076, filed Jun. 5, 2015, which claims the benefit of priority to U.S. Provisional Application 62/024,192 filed on Jul. 14, 2014, the disclosures of each of which are hereby incorporated by reference in their entireties.

FIELD OF THE INVENTION

The present invention relates to the compounds, processes for their preparation, pharmaceutical compositions containing them as active ingredient, methods for the treatment of disease states associated with cancers associated with protein kinases, to their use as medicaments for use in the production of inhibition of mTor, pi3k reducing effects in warm-blooded animals such as humans.

BACKGROUND OF THE INVENTION

The phosphatidylinositol 3-kinase (PI3K) signaling axis impacts on cancer cell growth, survival, motility, and metabolism, *J Clin Oncol* 28:1075-1083. The serine-threonine kinase mammalian target of rapamycin (mTor) also plays a major role in the regulation of protein translation, cell growth, and metabolism as well, *J Clin Oncol* 27:2278-2287. In addition to their physiologic role, several isoforms of the PI3K family are implicated in pathologic processes and diseases. Alterations of the mTor signaling pathway are common in cancer, and thus mTor is being actively pursued as a therapeutic target.

The present invention is based on the discovery of compounds of formula I that surprisingly inhibit the effect of mTor or pi3k/mTor. These are a new class of compounds that have advantageous pharmacological properties of value in the treatment of disease states associated with various cancers, such as: but not limited, tumors of colon, liver, lung, prostate, brain, breast; chronic myelocytic leukemia; macroglobulinemia; myelofibrosis; polycythemia vera; acute lymphoblastic leukemia; and other diseases, such as: but not limited, arthritis; autoimmune disease; bacterial infection; macular degeneration; multiple sclerosis; neurodegenerative.

Examples of compounds that are similar in structure or in kinase inhibition to those of the present invention are disclosed in the following literatures: WO2006122806, WO2008103636, WO2009155527, WO2004048365, WO07044698, and WO07044729.

SUMMARY OF THE INVENTION

The present invention relates to the compounds of formula I:

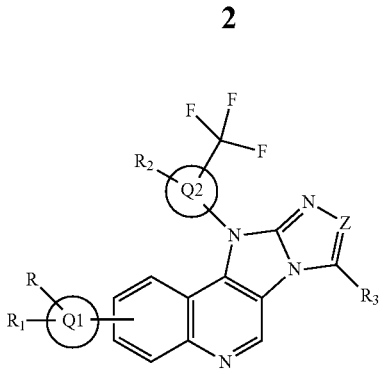

Formula I

Wherein
Q1 and Q2 are independently selected from an aryl, a 5-6 membered heterocyclyl or a 9-11 membered bicycloheterocyclyl; Q1 is a halogen when R and $R_1$ are not presented.
Z is N or C—R;
R and R1 are independently selected from H, halogen, halogen$C_1$-$C_6$alkyl, —$C_1$-$C_6$alkyl, —$OR_7$, or —$NR_7R_8$;
$R_2$ and $R_3$ are independently selected from H, halogen, —OH, —$C_1$-$C_6$alkyl, —$C_1$-$C_6$alkoxyl, —$C_1$-$C_6$alkenyl or —$C_1$-$C_6$alkynyl;
$R_4$ and $R_5$ are independently selected from H, halogen, halogen$C_1$-$C_6$alkyl, —$C_1$-$C_6$alkyl, —OH, —$C_1$-$C_6$alkoxyl, cycloalkyl; or both $R_4$ and $R_5$ can be combined together to form a 3-8 membered saturated or unsaturated ring that can be aliphatic cyclyl or heterocyclyl;
$R_7$ and $R_8$ are independently selected from H, halogen, —$C_1$-$C_6$alkyl, —$C_1$-$C_6$alkylOH, —$C_1$-$C_6$alkoxyl, —$C_1$-$C_6$alkylNR$_4$R$_5$, —C(=O)$C_1$-$C_6$alkyl, —C(=O)$C_1$-$C_6$alkyl-R$_4$R$_5$, —C(=O)$C_1$-$C_6$alkylOH, —C(=O)$C_1$-$C_6$alkoxyl, —C(=O)$C_1$-$C_6$alkylNR$_4$R$_5$, —C(=O)O$C_1$-$C_6$alkyl, —C(=O)O$C_1$-$C_6$alkylOH, —C(=O)O$C_1$-$C_6$alkoxyl, —C(=O)$C_1$-$C_6$alkylNR$_4$R$_5$, —C(=O)NR$_4$C$_1$-$C_6$alkyl, —C(=O)NR$_4$C$_1$-$C_6$al-kylOH, —C(=O)OCNR$_4$C$_1$-$C_6$alkoxyl, —C(=O)NR$_4$C$_1$-$C_6$alkylNR$_4$R$_5$;
or a pharmaceutically acceptable salt thereof.

DETAILED DESCRIPTION OF THE INVENTION

The present invention is directed to novel compounds of formula I: Wherein
Q1 and Q2 are independently selected from an aryl, a 5-6 membered heterocyclyl or a 9-11 membered bicycloheterocyclyl; preferably Q1 is independently selected from pyridinyl, pyrimidinyl, quinolinyl or quinazolinyl and Q2 is phenyl;
Q1 is a halogen when R and $R_1$ are not presented; preferably a Br or I;
Z is N or C—R; preferably is N;
R and $R_1$ are independently selected from H, halogen, halogen$C_1$-$C_6$alkyl, —$C_1$-$C_6$alkyl, —$OR_7$, or —$NR_7R_8$; preferably is H, or —$NR_7R_8$;
$R_2$ and $R_3$ are independently selected from H, —OH, —$C_1$-$C_6$alkyl, —$C_1$-$C_6$alkoxyl, —$C_1$-$C_6$alkenyl or —$C_1$-$C_6$alkynyl; preferably are independently selected from H, halogen or —$C_1$-$C_6$alkyl;
$R_4$ and $R_5$ are independently selected from H, halogen, halogen$C_1$-$C_6$alkyl, —$C_1$-$C_6$alkyl, —OH, —$C_1$-$C_6$alkoxyl, cycloalkyl; or both $R_4$ and $R_5$ can be combined together to form a 3-8 membered saturated or unsaturated ring that can be aliphatic cyclyl or heterocyclyl; preferably are halogen$C_1$-$C_6$alkyl, —$C_1$-$C_6$alkyl or both combined together to form a saturated aliphatic cyclyl or heterocyclyl ring;

$R_7$ and $R_8$ are independently selected from H, halogen, —$C_1$-$C_6$alkyl, —C(=O)$C_1$-$C_6$alkyl-$R_4R_5$, —$C_1$-$C_6$alkylOH, —$C_1$-$C_6$alkoxyl, —$C_1$-$C_6$alkylNR$_4$R$_5$, —C(=O)$C_1$-$C_6$alkyl, —C(=O)$C_1$-$C_6$alkylOH, —C(=O)$C_1$-$C_6$alkoxyl, —C(=O)$C_1$-$C_6$alkylNR$_4$R$_5$, —C(=O)O$C_1$-$C_6$alkyl, —C(=O)O$C_1$-$C_6$alkylOH, —C(=O)O$C_1$-$C_6$alkoxyl, —C(=O)O$C_1$-$C_6$alkylNR$_4$R$_5$, —C(=O)NR$_4$$C_1$-$C_6$alkyl, —C(=O)NR$_4$$C_1$-$C_6$alkylOH, —C(=O)NR$_4$$C_1$-$C_6$alkoxyl, —C(=O)NR$_4$$C_1$-$C_6$alkylNR$_4$R$_5$; preferably are independently selected from H, —C(=O)$C_1$-$C_6$alkyl, —$C_1$-$C_6$alkylNR$_4$R$_5$ or —C(=O)$C_1$-$C_6$alkylNR$_4$R$_5$;

or a pharmaceutically acceptable salt thereof.

The present invention is related to a compound of formula I which can be used in treating a neoplastic or proliferative or inflammatory disease, or a transplantation disorder, especially those caused by excess or inappropriate protein kinases; such as, but not limited, mTor or pi3k/mTor.

The present invention is related to the use of a compound of formula I in the manufacture of a medicament for use in the treatment of a neoplastic or proliferative or inflammatory disease, or a transplantation disorder, especially those caused by excess or inappropriate protein kinases, such as, but not limited, mTor or pi3k/mTor.

The term "halogen", as used herein, unless otherwise indicated, includes fluoro, chloro, bromo or iodo. such as fluoro and chloro.

The term "halogen$C_1$-$C_6$alkyl", as used herein, unless otherwise indicated, includes 1 to 6 halogen substituted alkyl, such as —CF$_3$.

The term "—$C_1$-$C_6$alkyl", as used herein, unless otherwise indicated, includes 1 to 6 saturated monovalent hydrocarbon radicals having straight or branched moieties, including, but not limited to, methyl, ethyl, n-propyl, iso-propyl, n-butyl, sec-butyl, tert-butyl and the like.

The term "—$C_1$-$C_6$alkenyl", as used herein, unless otherwise indicated, includes —$C_1$-$C_6$alkyl groups, as defined above, having at least one carbon-carbon double bond, such as —CH$_2$—CH=CH$_2$.

The term "—$C_1$-$C_6$alkynyl", as used herein, unless otherwise indicated, includes —$C_1$-$C_6$alkyl groups, as defined above, having at least one C—C triple bond, such as —CH$_2$—C≡CH.

The term "—$C_1$-$C_6$alkoxy", as used herein, unless otherwise indicated, includes —O$C_1$-$C_6$alkyl groups wherein lower alkyl is as defined above, such as methoxy and ethoxy.

The term "cycloalkyl", as used herein, unless otherwise indicated, includes cyclic radicals having from three to eight ring carbon atoms, including, but not limited to cyclopropyl, cyclobutyl, cyclopentyl, cyclohexyl, and the like. The cycloalkyl groups may be optionally substituted one or more times, substituents selected from the group defined above as substituents for aryl, preferably halogen, —$C_1$-$C_6$alkyl.

The term "aryl", as used herein, unless otherwise indicated, includes an organic radical derived from an aromatic hydrocarbon by removal of one hydrogen, such as phenyl or naphthyl, preferably phenyl, and is unsubstituted or substituted by one or two substituents, selected from halogen, halogeno-lower alkyl, lower alkyl, lower alkenyl, lower alkynyl, cyano, lower alkylcyano, hydroxy, lower alkoxy, carboxy, carboxyalkyl, amino, carbamoyl, cabamate, ureido, mercapto, sulfo, lower alkylsulfinyl, lower alkanesulfonyl, sulfonamide; aryl includes one aromatic ring fused with an aliphatic ring, such as a saturated or partially saturated ring, such as tetrahydronaphthyl.

The term "heterocyclyl", as used herein, unless otherwise indicated, includes non-aromatic saturated or partial saturated single and fused rings suitably containing up to four heteroatoms in each ring, each of which independently selected from O, N and S, and which rings, may be unsubstituted or substituted independently by, for example, up to three substituents. Each heterocyclic ring suitably has from 4 to 7, preferably 5 or 6, ring atoms. A fused heterocyclic ring system may include carbocyclic rings and need include only one heterocyclic ring which may be partially saturated or saturated. The heterocyclyl includes mono, bicyclic and tricyclic heteroaromatic ring systems comprising up to four, preferably 1 or 2, heteroatoms each selected from O, N and S. Each ring may have from 4 to 7, preferably 5 or 6, ring atoms. A bicyclic or tricyclic ring system may include a carbocyclic ring. Carbocyclic ring includes cycloalkyl, cycloalkenyl or aryl ring. examples of heterocyclyl groups include but not limited: azetidine, pyrrolidine, pyrrolidione, piperidine, piperidinone, piperazine, morpholine, oxetane, tetrahydro-furan, tetrahydropyran, imidazolidine, pyrazolidine and hydantoin, pyrrole, indole, pyrazole, inda-zole, trizole, benzotrizole, imidazole, benzoimdazole, thiophene, benzothiophene, thiozole, benzo-thiozole, furan, benzofuran, oxazole, bezoxazole, isoxazole, tetrazole, pyridine, pyrimidine, trizine, quinoline, isoquinoline, quinazoline, indoline, indolinone, benzotetrahydrofuran, tetrahydroquino-line, tetrahydroisoquinoline, methylene-dioxyphenyl. The heterocyclic and heterocyclic rings may be substituted and substituents selected from the group defined above as substituents for aryl.

The term "aliphatic cyclyl", as used herein, unless otherwise indicated, includes cyclic saturated or unsaturated carbon compounds, excluding aromatic compounds, such as cyclopropyl or cyclopropene and the like.

In vitro kinase inhibition activities included Pi3k and mTor activities can be tested with Millipore/Merck KGA of Europe in their kinases panel screening. Animal antitumor activity testing can be conducted by various cancer xenograft models for a compound of formula I.

A compound of formula I can be administered alone or in combination with one or more other therapeutic agents, including but not limited 17a-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, chlorotrianisene, Hydroxyprogesterone, Aminoglutethimide, Estramustine, Medroxyprogesteroneacetate, Leuprolide, Flutamide, Toremifene, Zoladex, matrix metalloproteinase inhibitors, Suitable EGFR inhibitors include gefitinib, erlotinib, and cetuximab. Pan Her inhibitors include canertinib, EKB-569, and GW-572016. VEGF inhibitors, such as Avastin, ZD6474 and BAY-43-9006, SU11248, CP-547632 and CEP-7055. Also included are Src inhibitors as well as Casodex@ (bicalutamide, Astra Zeneca), Tamoxifen, MEK-1 kinase inhibitors, MAPK kinase inhibitors, and PDGF inhibitors, such as imatinib. Also included are IGF1R inhibitors, inhibitors of non-receptor and receptor tyrosine kinases, and inhibitors of integrin signaling Also included are anti-angiogenic and antivascular agents which, by interrupting blood flow to solid tumors, render cancer cells quiescent by depriving them of nutrition. Additional cytotoxic agents include, melphalan, hexamethyl melamine, thiotepa, cytarabin, idatrexate, trimetrexate, dacarbazine, L-asparaginase, camptothecin, topotecan, bicalutamide, flutamide, leuprolide, pyridobenzoindole derivatives, interferons, and interleukins. Additional anticancer agents include microtubule-stabilizing agents such as paclitaxel, docetaxel, (Ser. No. 09/712,352 filed on Nov. 14, 2000), C-4 methyl carbonate paclitaxel, epothilone A, epothilone B, epothilone C, epothilone D, desoxyepothilone A, desoxyepothilone and microtubule-disruptor agents. Also suitable are CDK inhibitors, an antiproliferative cell cycle inhibitor, epidophyllotoxin; an antineoplastic enzyme; a topoisomerase inhibitor; procarbazine; mitoxantrone; platinum coordination complexes such as cis-platin and carboplatin; biological response modifiers; growth inhibitors; antihormonal therapeutic agents; leucovorin; tegafur; and haematopoietic growth factors. Castration, which also renders androgen dependent carcinomas non-proliferative, may also be utilized. The possible combination therapy takes the form of fixed combinations or administration of a compound of the invention and one or more other therapeutic agents being staggered or given independently of one another, or the combined administration of fixed combinations and one or more other therapeutic agents.

A compound of formula I can besides or in addition be administered especially for tumor therapy in combination with chemotherapy, radiotherapy, surgical intervention, or a combination of these. Long term therapy is equally possible as is adjuvant therapy in the context of other treatment strategies, as described above. Other possible treatments are therapy to maintain the patient's status after tumor regression, or even chemopreventive therapy, for example in patients at risk. A compound of Formula I is useful in the treatment of a variety of cancers, including, but not limited to, the following: (a) carcinoma, including that of the bladder, breast, colon, kidney, liver, lung, including small cell lung cancer, esophagus, gall bladder, ovary, pancreas, stomach, cervix, thyroid, prostate, and skin, including squamous cell carcinoma; (b) hematopoietic tumors of lymphoid lineage, including leukemia, acute lymphocytic leukemia, acute lymphoblastic leukemia, B-cell lymphoma, T-cell lymphoma, Hodgkin's lymphoma, non-Hodgkins lymphoma, hairy cell lymphoma and Burkett's lymphoma; (c) hematopoietic tumors of myeloid lineage, including acute and chronic myelogenous leukemias, myelodysplastic syndrome and promyelocytic leukemia; (d) tumors of mesenchymal origin, including fibrosarcoma and rhabdomyosarcoma; (e) tumors of the central and peripheral nervous system, including astrocytoma, neuroblastoma, glioma and schwannomas; and (f) other tumors, including melanoma, seminoma, teratocarcinoma, osteosarcoma, xenoderoma pigmentosum, keratoctanthoma, thyroid follicular cancer and Kaposi's sarcoma.

A compound according to the invention is not only for management of humans, but also for the treatment of other warm-blooded animals, for example of commercially useful animals. Such a compound may also be used as a reference standard in the test systems described above to permit a comparison with other compounds.

Salts are especially the pharmaceutically acceptable salts of compounds of formula I. Suitable pharmaceutically acceptable salts will be apparent to those skilled in the art and include those described in J. Pharm. Sci., 1977, 66, 1-19, such as acid addition salts formed with inorganic acid e.g. hydrochloric, hydrobromic, sulphuric, nitric or phosphoric acid; and organic acids e.g. succinic, maleic, acetic, fumaric, citic, tartaric, benzoic, p-toluenesulfonic, methanesulfonic or naphthalenesulfonic acid. Other salts may be used, for example in the isolation or purification of compounds of formula I and are included within the scope of this invention.

The compounds of this invention may be in crystalline or non-crystalline form, and, if crystalline, may optionally be hydrated or solvated. This invention includes within its scope stoichiometric hydrates as well as compounds containing variable amount of water.

The invention extends to all isomeric forms including stereoisomers and geometric isomers of the compounds of formula I including enantiomers and mixtures thereof e.g. racemates. The different isomeric forms may be separated or resolved one from the other by conventional methods, or any given isomer may be obtained by conventional synthetic methods or by stereospecific or asymmetric syntheses.

Those skilled in the art will recognize various synthetic methodologies that may be employed to prepare non-toxic pharmaceutically acceptable prodrugs of the compounds encompassed by Formula I. Those skilled in the art will recognize a wide variety of non-toxic pharmaceutically acceptable solvents that may be used to prepare solvates of the compounds of the invention, such as water, ethanol, mineral oil, vegetable oil, and dimethylsulfoxide.

The compounds of general Formula I may be administered orally, topically, parenterally, by inhalation or spray or rectally in dosage unit formulations containing conventional non-toxic pharmaceutically acceptable carriers, adjuvants and vehicles. Oral administration in the form of a pill, capsule, elixir, syrup, lozenge, troche, or the like is particularly preferred. The term parenteral as used herein includes subcutaneous injections, intradermal, intravascular (e.g., intravenous), intramuscular, spinal, intrathecal injection or like injection or infusion techniques. In addition, there is provided a pharmaceutical formulation comprising a compound of general Formula I and a pharmaceutically acceptable carrier. One or more compounds of general Formula I may be present in association with one or more non-toxic pharmaceutically acceptable carriers and/or diluents and/or adjuvants and if desired other active ingredients. The pharmaceutical compositions containing compounds of general Formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl disterate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The compounds may also be administered in the form of suppositories for rectal or vaginal administration of the drug. These compositions can be prepared by mixing the drug with a suitable non-irritating excipient which is solid at ordinary temperatures but liquid at the rectal or vaginal temperature and will therefore melt in the rectum or vagina to release the drug. Such materials include cocoa butter and polyethylene glycols.

The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of the invention may also be administered transdermally using methods known to those skilled in the art (see, for example: Chien; "Transdermal Controlled Systemic Medications"; Marcel Dekker, Inc.; 1987. Lipp et al. WO 94/04157).

Compounds of general Formula I may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

For administration to non-human animals, the composition may also be added to the animal feed or drinking water. It will be convenient to formulate these animal feed and drinking water compositions so that the animal takes in an appropriate quantity of the composition along with its diet. It will also be convenient to present the composition as a premix for addition to the feed or drinking water.

For all regimens of use disclosed herein for compounds of formula I, the daily oral dosage regimen will preferably be from 0.01 to 200 mg/kg of total body weight. The daily dosage for administration by injection, including intravenous, intramuscular, subcutaneous and parenteral injections, and use of infusion techniques will preferably be from 0.01 to 200 mg/kg of total body weight. The daily rectal dosage regimen will preferably be from 0.01 to 200 mg/kg of total body weight. The daily vaginal dosage regimen will preferably be from 0.01 to 200 mg/kg of total body weight. The daily topical dosage regimen will preferably be from 0.01 to 200 mg/kg of total body weight administered between one to four times daily. The transdermal concentration will preferably be that required to maintain a daily dose of from 0.01 to 200 mg//kg of total body weight. The daily inhalation dosage regimen will preferably be from 0.01 to 200 mg/kg of total.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

Preferred compounds of the invention will have certain pharmacological properties. Such properties include, but are not limited to oral bioavailability, low toxicity, low serum protein binding and desirable in vitro and in vivo half-lives. Assays used to predict bioavailability include transport across human intestinal cell monolayers, including Caco-2 cell monolayers. Toxicity to cultured hepatocyctes may be used to predict compound toxicity. Serum protein binding may be predicted from albumin binding assays. Compound half-life is inversely proportional to the frequency of dosage of a compound. In vitro half-lifes of compounds may be predicted from assays of microsomal half-life.

Representative illustrations of the preparation of the present invention are given in Scheme I-Scheme II. Those having skill in the art will recognize that the starting materials may be varied and additional steps may be employed to produce compounds encompassed by the present invention.
Scheme I
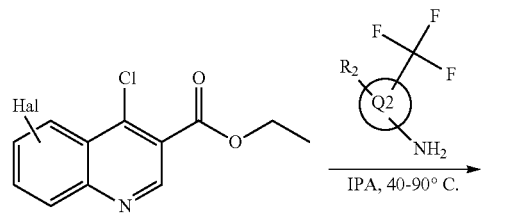
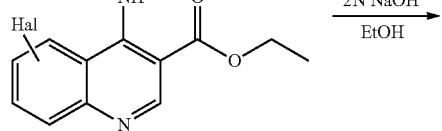
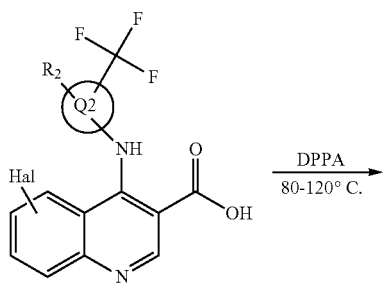
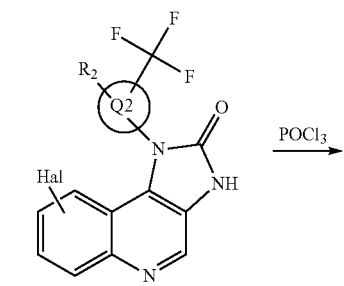
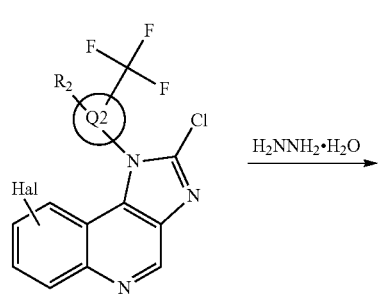
-continued
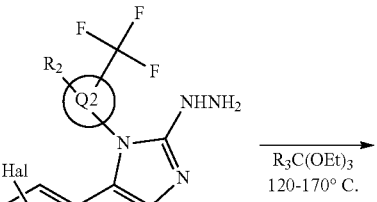
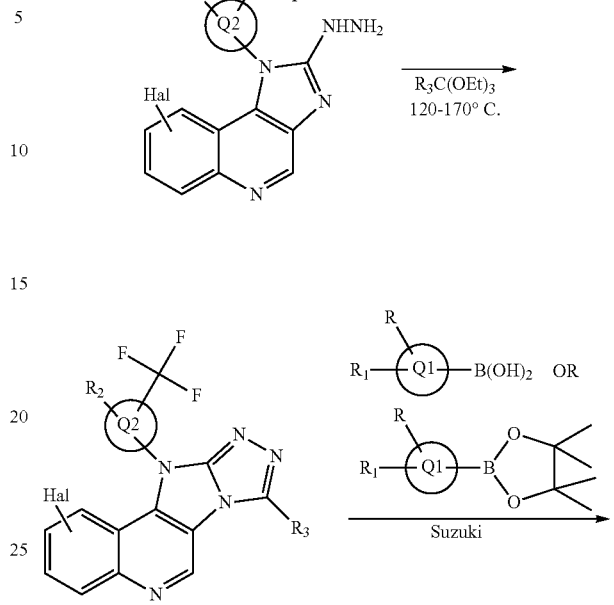
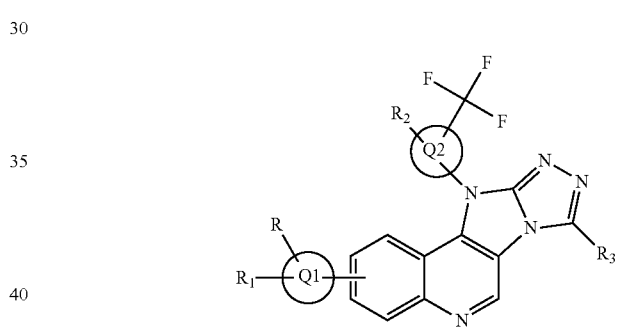
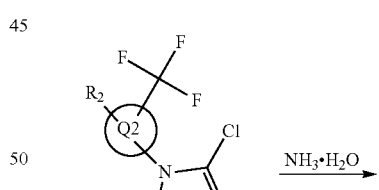
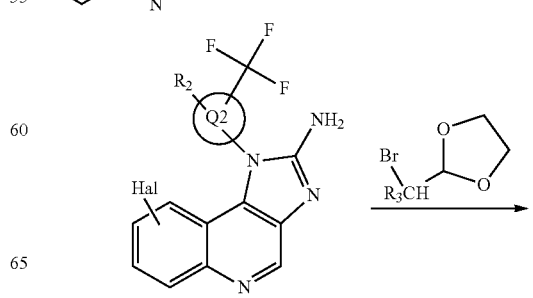

11
-continued
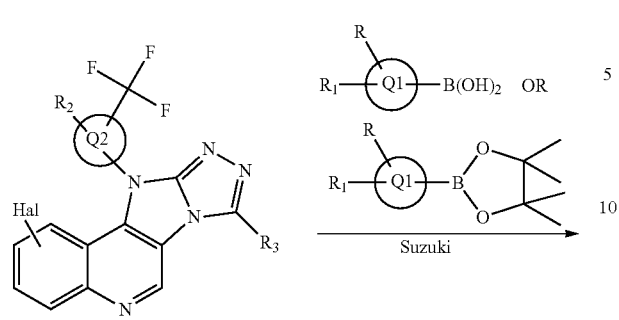
Suzuki
12
-continued
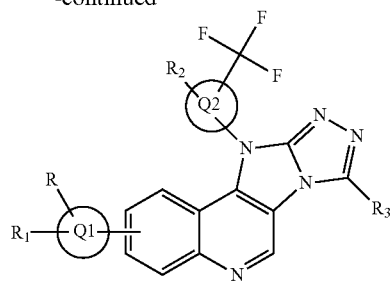
Hal is a halogen, preferably Br and I;
Q1, Q2, R, R1, R2, R3, R4, R5, R7, R8 are defined as above.
Scheme II
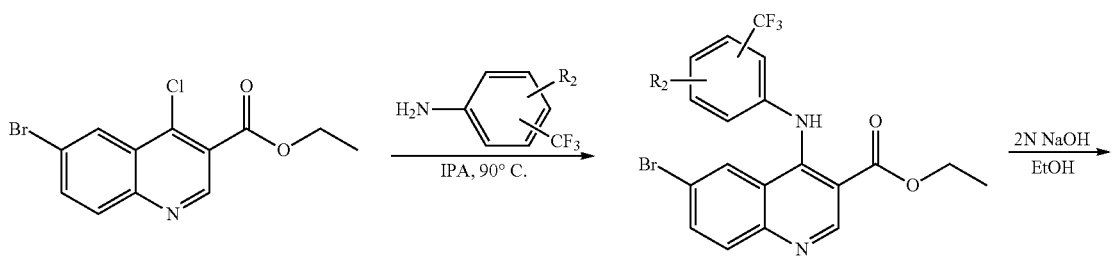
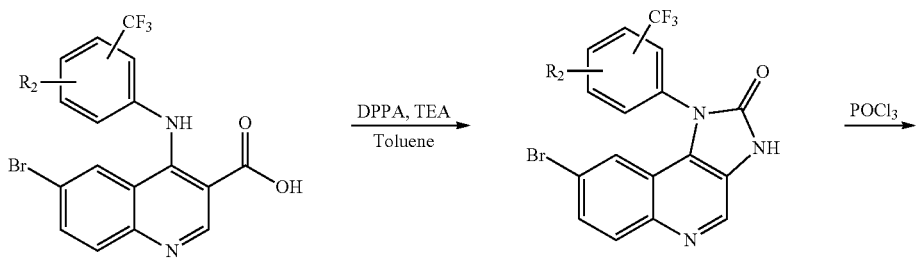
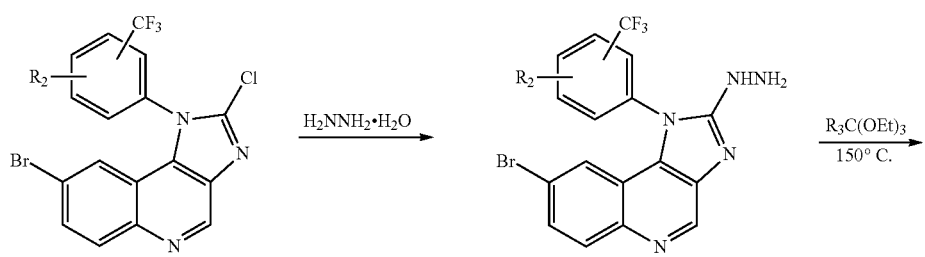

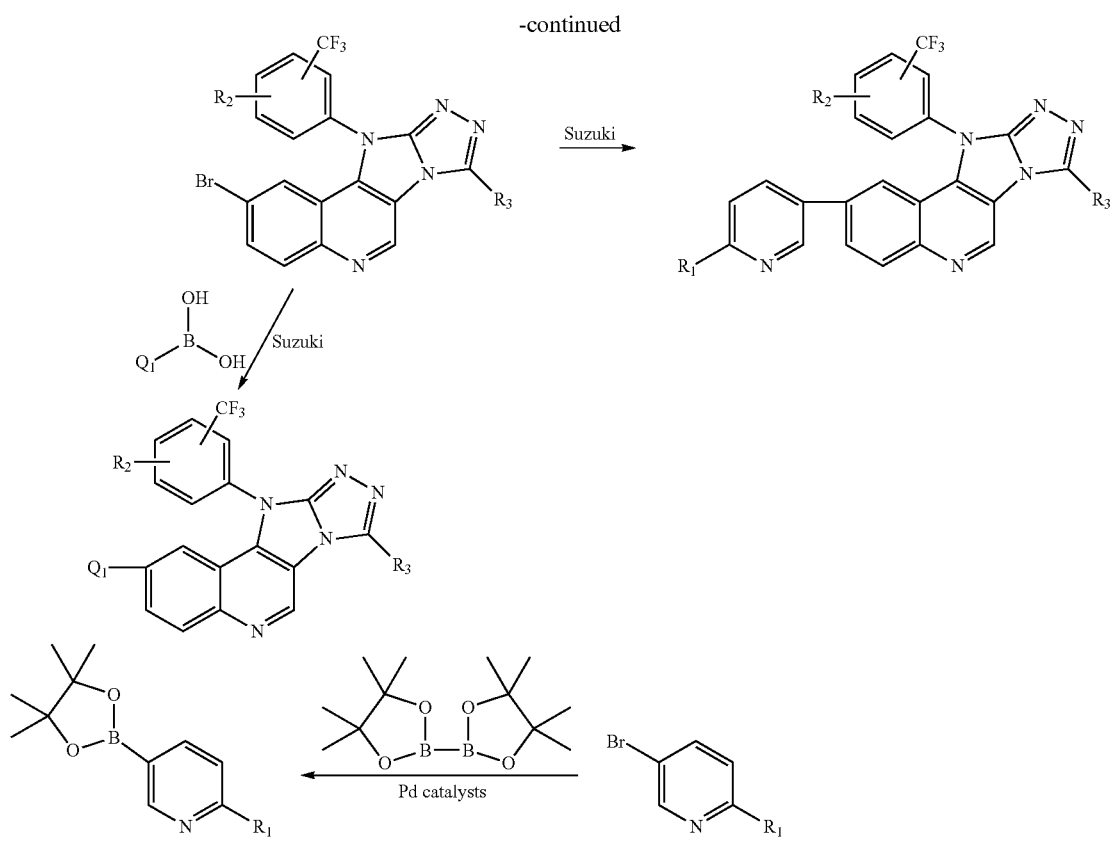

R1 is selected from:
—NH2, —NHCH3, —N(CH3)2, —NHCOCH3, —NHCO(CH2)$_n$CH3, —NHCO(CH2)$_n$NH2,
—NHCO(CH2)$_n$NHCH3, —NHCO(CH2)$_n$N(CH3)2, —NHCO(CH2)$_n$-Pyrrolidine, —NHCO(CH2)$_n$-Piperazine,
—NHCO(CH2)$_n$-Morpholine, —NH(CH2)$_n$NHCH3, —NH(CH2)$_n$N(CH3)2, —NH(CH2)$_n$-Pyrrolidine,
—NH(CH2)$_n$-Piperazine, —NH(CH2)$_n$-Morpholine;

n = 1, 2, 3 or 4;
R2 is H, halogen or —$C_1$-$C_6$alkyl; R3 is H or —$C_1$-$C_6$alkyl;
Q1 is independently selected from pyridine, pyrimidine, quinoline or quinazoline;

The following examples of Formula II, but not limited, can also be prepared similarly according to the methods described in Scheme I-Scheme II.

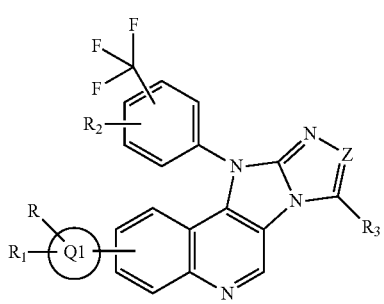

Formula II

Wherein
Q1 is independently selected from an aryl, a 5-6 membered heterocyclyl or a 9-11 membered bicycloheterocyclyl; preferably Q1 is independently selected from pyridinyl, pyrimidinyl, quinolinyl or quinazolinyl;

Q1 is a halogen when R and $R_1$ are not presented; preferably a Br or I;
Z is N or C—R; preferably is N;
R and $R_1$ are independently selected from H, halogen, halogen$C_1$-$C_6$alkyl, —$C_1$-$C_6$alkyl, —$OR_7$, or —$NR_7R_8$; preferably is H, or —$NR_7R_8$
$R_2$ and $R_3$ are independently selected from H, —OH, —$C_1$-$C_6$alkenyl or —$C_1$-$C_6$alkynyl; preferably are independently selected from H, halogen or —$C_1$-$C_6$alkyl;
$R_4$ and $R_5$ are independently selected from H, halogen$C_1$-$C_6$alkyl, —$C_1$-$C_6$alkyl or both combined together to form a saturated aliphatic cyclyl or heterocyclyl ring;
$R_7$ and $R_8$ are independently selected from H, halogen, —$C_1$-$C_6$alkyl, —$C_1$-$C_6$alkylNR$_4$R$_5$, —C(=O)$C_1$-$C_6$alkyl, —C(=O)$C_1$-$C_6$alkyl-R$_4$R$_5$, —C(=O)$C_1$-$C_6$alkylOH, —C(=O)$C_1$-$C_6$alkoxyl, —C(=O)$C_1$-$C_6$alkylNR$_4$R$_5$, —C(=O)O$C_1$-$C_6$alkyl, —C(=O)O$C_1$-$C_6$alkylOH, —C(=O)O$C_1$-$C_6$alkoxyl, —C(=O)O$C_1$-$C_6$alkylNR$_4$R$_5$, —C(=O)NR$_4$$C_1$-$C_6$alkyl, —C(=O)NR$_4$$C_1$-$C_6$alkylOH, —C(=O)—NR$_4$$C_1$-$C_6$alkoxyl, —C(=O)NR$_4$$C_1$-$C_6$alkylNR$_4$R$_5$; preferably are independently selected from H, —C(=O)$C_1$-$C_6$alkyl, —$C_1$-$C_6$alkylNR$_4$R$_5$ or —C(=O)$C_1$-$C_6$alkylNR$_4$R$_5$;
or a pharmaceutically acceptable salt thereof.

The following compounds or a pharmaceutically acceptable salt thereof, but not limited, can also be prepared similarly according to the methods described in Scheme I-Scheme II. They are also tested for the inhibitions on mTor or pi3k kinases, or tumor cell lines.

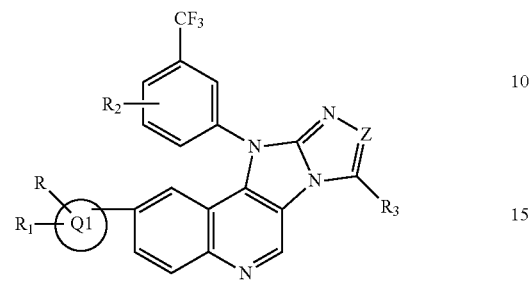

Wherein

| R$_1$-Q1(R) | R2 | R3 | Mass (Found) (M + 1) | mTor % activity @0.03 μM | pi3K % activity @0.03 μM |
|---|---|---|---|---|---|
| 3-pyridine | 4-F | CH2CH3 | 477 | 73 | |
| 3-pyridine | 4-F | H | 449 | 17 | 81 |
| 3-quinoline | 4-F | H | 499 | 25 | |
| 3-quinoline | 4-Cl | H | 515 | 11 | 84 |
| 3-pyridine | 4-Cl | H | 465 | 19 | 77 |
| 5-pyridin-2-amine | 4-Cl | H | 480 | -19 | 38 |
| 3-Flurophenyl | 4-Cl | H | 482 | 46 | |
| 3,4-Diflurophenyl | 4-Cl | H | 500 | 31 | |
| 2-Flurophenyl | 4-Cl | H | 482 | 55 | |
| N-(5-pyridin-2-yl)acetamide | 4-Cl | H | 522 | 5 | |
| 3-quinoline | H | H | 481 | -5 | 68 |
| 3-pyridine | H | H | 431 | 0 | 70 |
| 3-quinoline | 5-CF3 | H | 549 | 0 | |
| 3-quinoline | 5-F | H | 499 | -8 | |
| 3-quinoline | 6-F | H | 499 | 0 | |
| 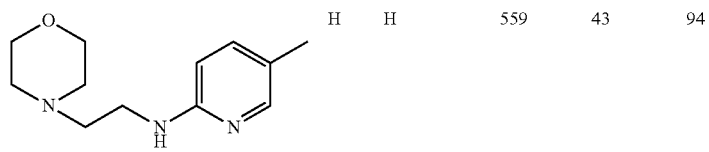 | H | H | 559 | 43 | 94 |
| 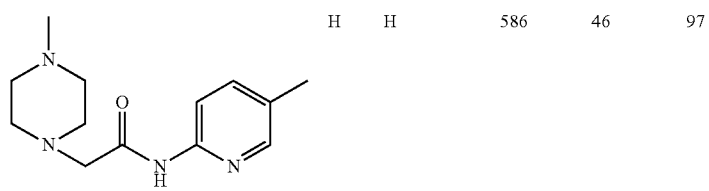 | H | H | 586 | 46 | 97 |
| 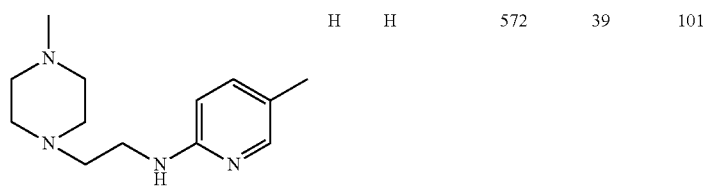 | H | H | 572 | 39 | 101 |
| 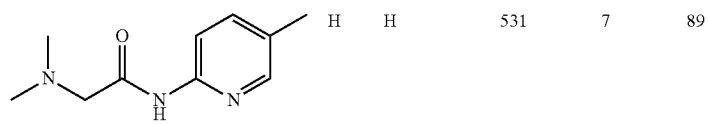 | H | H | 531 | 7 | 89 |

-continued
| | R2 | R3 | Mass (Found) (M + 1) | mTor % activity @0.03 µM | pi3K % activity @0.03 µM |
|---|---|---|---|---|---|
| 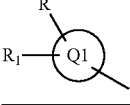 | H | H | 517 | 21 | 98 |
| 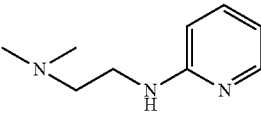 | H | H | 573 | 31 | 95 |
| 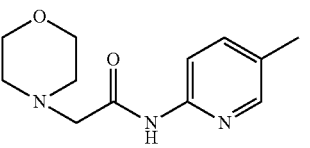 | H | H | 517 | 7 | 55 |
| 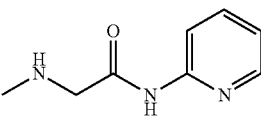 | H | H | 503 | 9 | 52 |
| 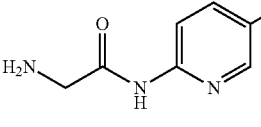 | H | H | 556 | 11 | 90 |
| 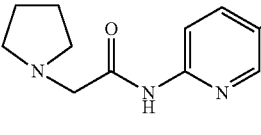 | H | H | 543 | 4 | 101 |
| 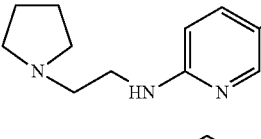 | H | H | 490 | 8 | 96 |
| 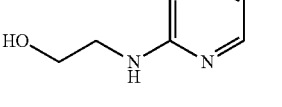 | H | H | 504 | −3 | 92 |
| 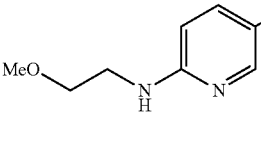 | 4-Cl | H | 537 | 9 | 83 |
| 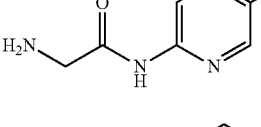 | 4-Cl | H | 565 | 15 | |
| 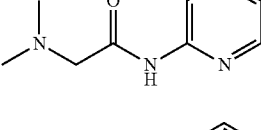 | 4-Cl | H | 551 | 24 | 95 |

-continued
| | R2 | R3 | Mass (Found) (M + 1) | mTor % activity @0.03 μM | pi3K % activity @0.03 μM |
|---|---|---|---|---|---|
| 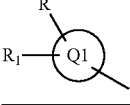 | 4-Cl | H | 621 | −4 | 74 |
| 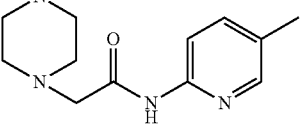 | 4-Cl | H | 605 | 32 | 81 |
| 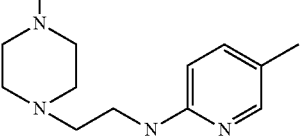 | 4-Cl | H | 608 | 17 | 82 |
| 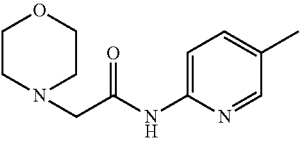 [SMILES: Cc1ccc(NC(=O)CN2CCOCC2)nc1] | 4-Cl | H | 620 | 57 | |
| 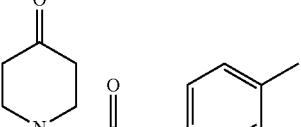 | 4-Cl | H | 622 | 14 | |
| 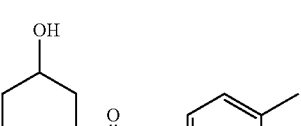 | 4-Cl | H | 592 | 4 | 82 |
| 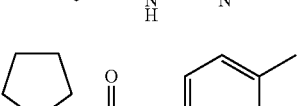 | 4-Cl | H | 578 | 15 | 98 |
| 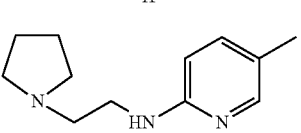 | 4-Cl | H | 594 | 20 | 93 |
| 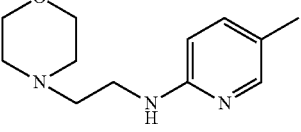 | 4-Cl | H | 538 | −5 | 87 |

-continued

| R2 | R3 | Mass (Found) (M + 1) | mTor % activity @0.03 μM | pi3K % activity @0.03 μM |
|---|---|---|---|---|
| 4-Cl | H | 524 | −4 | 82 |

(with R₁ = HO-CH₂CH₂-NH- attached to 5-methylpyridin-2-yl)

| | R2 | R3 | | | |
|---|---|---|---|---|---|
| Br | 4-Cl | H | | | |
| Br | H | H | | | |
| Br | 5-CF3 | CH3 | | | |
| Br | 5-F | CH3 | | | |
| Br | 6-F | CH2CH3 | | | |
| Br | 4-F | CH2CH3 | | | |

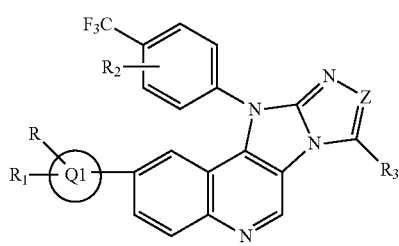

Wherein

| | R2 | R3 | Mass (Found) (M + 1) | mTor % activity @0.03μM | pi3K % activity @0.03μM |
|---|---|---|---|---|---|
| 3-quinoline | H | H | 481 | 68 | 99 |

In some cases protection of certain reactive functionalities may be necessary to achieve some of above transformations. In general the need for such protecting groups will be apparent to those skilled in the art of organic synthesis as well as the conditions necessary to attach and remove such groups. Those skilled in the art will recognize that in certain instances it will be necessary to utilize different solvents or reagents to achieve some of the above transformations.

The disclosures in this application of all articles and references, including patents, are incorporated herein by reference in their entirety.

The invention is illustrated further by the following examples, which are not to be construed as limiting the invention in scope or spirit to the specific procedures described in them.

The starting materials are and various intermediates may be obtained from commercial sources, prepared from commercially available organic compounds, or prepared using well known synthetic methods. Representative methods for preparing intermediates of the invention are set forth below in the examples. The following abbreviations have been used and others are all standard chemical formula representation.

DCM: Dichloromethane, DMF: N,N-dimethylformamide, HOBt: 1-hydroxy-benzotriazole hydrate, EDC: 1-(3-dimethylaminopropyl)-3-ethylcarbodiimide hydrochloride, DPPA: Diphenyl phosphoryl azide, (dppf)₂PdCl₂:[1,1'-Bis (diphenylphosphino)ferrocene]dichloropalla-dium(II), g: gram, mg: milligram, ml: milliliter.

EXAMPLE 1

Preparation of 16-(3-(trifluoromethyl)phenyl)-4-(pyridin-3-yl)-8,11,13,14,16-pentaazatetracyclo-[8.6.0.0$^{2,7}$.0$^{11,15}$]hexadeca-1(10),2,4,6,8,12,14-heptaene A mixture of 4-bromoaniline (17.2 g, 0.1 mol) and diehylethoxymethylenemalonate (21.6 g, 0.1 mol) was heated at 130° C. for 2 hours (the starting materials were consumed by TLC monitoring). After cooling to room temperature, the reaction was concentrated under reduced pressure to give diethyl 2-((4-bromophenylamino)methylene)malonate (compound 1, 30.5 g, 89%) as a yellowish solid.

To a preheated refluxing di-phenol ether (50 ml), was added compound 1 (30.5 g, 0.0892 mol) in about 15 min. The resulting mixture was continue to heat at reflux until the bubbling stopped in about 1 to 2 hours. After cooling to room temperature, the solid was collected and dried to give ethyl 6-bromo-4-oxo-1,4-dihydroquinoline-3-carboxylate (compound 2, 25.4 g, 88%) as an off white solid.

Compound 2 (19.4 g, 0.06 mol) was suspended in POCl₃ (45 ml) and heated at reflux for 1 hour. The excess solvent was evaporated under reduced pressure and the deep brown residue was taken up in dichloromethane (150 ml) and washed sequentially by water (100 ml), saturated sodium bicarbonate (100 ml), and brine (100 ml). The organic phase was dried over sodium sulfate, the solid was filtered off and the filtrate was concentrated to give ethyl 6-bromo-4-chloroquinoline-3-carboxylate (compound 3, 17.67 g, 93.8%) as a yellowish solid.

A mixture of compound 3 (5 g, 0.0159 mol) and 3-aminobenzotrifluoride (compound 4, 2 ml, 0.016 mol) in 2-propanol (50 ml) was heated at reflux for 30 min. The precipitated solid was collected and dried to give ethyl 6-bromo-4-(4-(3-trifluoromethyl)-phenylamino)quinoline-3-carboxylate (compound 5, 6.8 g) as a yellow solid.

The compound 5 (4.5 g, 0.01 mol) was suspended in ethanol (30 ml) was added 2N sodium hydroxide (25 ml) at room temperature. The resulting mixture was heated at reflux for 2 hours. The reaction solution was concentrated under reduced pressure and the residue was dissolved in water (20 ml) and methanol (2 ml). The solution was acidified to PH 3 by acetic acid, and the precipitated solid was collected and washed thoroughly by water then dried to give 6-bromo-4-(4-(3-trifluoromethyl)phenylamino)quinoline-3-carboxylic acid (compound 6, 3.9 g, 92.8%) as a bright yellow solid.

To a suspension of compound 6 (3.7 g, 8.8 mmol) in toluene (30 ml) was added DMF (1 ml), triethylamine (3.7 ml, 26.6 mmol) and DPPA (4.9 g, 17.8 mmol). The resulting mixture was heated at 85-95° C. for 4 hours then cooled to room temperature. The solid was collected, washed with hexanes, and dried to give 8-bromo-1-(3-(trifluoromethyl)phenyl)-1H-imidazo[4,5-c]quinolin-2(3H)-one (compound 7, 2.57 g) as a light tan solid.

To a suspension of compound 7 (2.5 g, 6.1 mmol) in phosphorus oxychloride (17 ml) was added N,N-diisopropylethylamine (7.7 ml) and the mixture was heated at reflux for 48 hours. After cooling to room temperature, the excess solvents were evaporated under reduced pressure and the residue was taken up in dichloromethane (50 ml), then organic phase was washed sequentially by ice water (50 ml), saturated sodium bicarbonate (50 ml), and brine (50 ml). The organic phase was dried over sodium sulfate, the solid was filtered off and the filtrate was concentrated to give 8-bromo-2-chloro-1-(3-(trifluoromethyl)phenyl)-1H-imidazo[4,5-c]quinoline (compound 8, 2.5 g, 89%) as a brown solid.

To a suspension of compound 8 (2.5 g, 5.9 mmol) in ethanol (20 ml) was added hydrazine monohydrate (5.7 ml), the resulting mixture was heated at reflux for 3 hours. After cooling to room temperature, the reaction solution was concentrated under reduced pressure, then the residue was taken up in dichloromethane (50 ml) and was washed sequentially by water (50 ml), and brine (50 ml). The organic phase was dried over sodium sulfate, the solid was filtered off and the filtrate was concentrated to give 8-bromo-2-hydrazinyl-1-(3-(trifluoromethyl)phenyl)-1H-imidazo[4,5-c]quinoline as a light blue solid (compound 9, 2.1 g, 91%).

To a 38 ml sealed tube was charged with compound 9 (1.5 g, 3.6 mmol), triethylorthoformate (12 ml), and hydrogen chloride (37%, 5 drops), the sealed tube was sealed and heated at reflux for 10 hours. After cooling to room temperature, the precipitated solid was collected and dried to give to 4-bromo-16-[3-(trifluoromethyl)phenyl]-8,11,13,14,16-pentaazatetracyclo[8.6.0.0$^{2,7}$.0$^{11,15}$]hexade-ca-1(10),2,4,6,8,12,14-heptaene (compound 10, 1 g) as a gray solid.

To a 50 ml of round flask was charged with compound 10 (1 g, 2.3 mmol), 3-pyridineboronic acid (566 mg, 4.6 mmol), bis(triphenylphosphine)palladium(II)chloride (16 mg, 0.023 mmol), 2N sodium carbonate monohydrate (3 ml) and dioxane (10 ml), then the mixture was degassed three times, filled with nitrogen, and heated at 110° C. for 24 hours. The reaction mixture was taken up in dichloromethane (50 ml), washed with water (30 ml), and brine (30 ml), then dried over sodium sulfate, the solid was filtered off, the filtrate was concentrated under reduced pressure and the residue was purified by column to give the titled compound as a light brown solid (1 g).

EXAMPLE 2

Preparation of 12-ethyl-16-[4-fluoro-3-(trifluoromethyl)phenyl]-4-8,11,13,14,16-pentaazatetracyclo[8.6.0.0$^{2,7}$.0$^{11,15}$]hexadeca-1(10),2,4,6,8,12,14-heptaene The titled compound was similarly prepared by the method described in Example 1 using 4-fluoro-3-trifluoromethyl aniline and triethylothroproponate.

The following compound examples were prepared analogously according to the methods described in Example 1 by using different anilines and different boronic acids.

4-bromo-16-[4-chloro-3-(trifluoromethyl)phenyl]-8,11,13,14,16-pentaazatetracyclo-[8.6.0.0$^{2,7}$.0$^{11,15}$]hexadeca-1(10),2,4,6,8,12,14-heptaene;

16-[3,5-bis(trifluoromethyl)phenyl]-4-bromo-8,11,13,14,16-pentaazatetracyclo[8.6.0.0$^{2,7}$.0$^{11,15}$]-hexadeca-1(10),2,4,6,8,12,14-heptaene;

4-bromo-16-[3-fluoro-5-(trifluoromethyl)phenyl]-8,11,13,14,16-pentaazatetracyclo-[8.6.0.0$^{2,7}$.0$^{11,15}$]hexadeca-1(10),2,4,6,8,12,14-heptaene;

4-bromo-16-[2-fluoro-5-(trifluoromethyl)phenyl]-8,11,13,14,16-pentaazatetracyclo-[8.6.0.0$^{2,7}$.0$^{11,15}$]hexadeca-1(10),2,4,6,8,12,14-heptaene;

4-bromo-16-[4-fluoro-3-(trifluoromethyl)phenyl]-8,11,13,14,16-pentaazatetracyclo-[8.6.0.0$^{2,7}$.0$^{11,15}$]hexadeca-1(10),2,4,6,8,12,14-heptaene;

12-ethyl-16-[4-fluoro-3-(trifluoromethyl)phenyl]-4-(quinolin-3-yl)-8,11,13,14,16-pentaazate-tracyclo[8.6.0.0$^{2,7}$.0$^{11,15}$]hexadeca-1(10),2,4,6,8,12,14-heptaene;

16-[4-chloro-3-(trifluoromethyl)phenyl]-4-(quinolin-3-yl)-8,11,13,14,16-pentaazatetracyclo-[8.6.0.0$^{2,7}$.0$^{11,15}$]hexadeca-1(10),2,4,6,8,12,14-heptaene;

16-[4-chloro-3-(trifluoromethyl)phenyl]-4-(pyridin-3-yl)-8,11,13,14,16-pentaazatetracyclo-[8.6.0.0$^{2,7}$.0$^{11,15}$]hexadeca-1(10),2,4,6,8,12,14-heptaene;

5-{16-[4-chloro-3-(trifluoromethyl)phenyl]-8,11,13,14,16-pentaazatetracyclo-[8.6.0.0$^{2,7}$.0$^{11,15}$]hexadeca-1(10),2,4,6,8,12,14-heptaen-4-yl}pyridin-2-amine;

16-[4-chloro-3-(trifluoromethyl)phenyl]-4-(3-fluorophenyl)-3-yl)-8,11,13,14,16-pentaazatetracyclo-[8.6.0.0$^{2,7}$.0$^{11,15}$]hexadeca-1(10),2,4,6,8,12,14-heptaene;

16-[4-chloro-3-(trifluoromethyl)phenyl]-4-(3,4-difluorophenyl)-8,11,13,14,16-pentaazatetra-cyclo-[8.6.0.0$^{2,7}$.0$^{11,15}$]hexadeca-1(10),2,4,6,8,12,14-heptaene;

16-[4-chloro-3-(trifluoromethyl)phenyl]-4-(2-fluorophenyl)-8,11,13,14,16-pentaazatetracyclo-[8.6.0.0$^{2,7}$.0$^{11,15}$]hexadeca-1(10),2,4,6,8,12,14-heptaene;

N-(5-{16-[4-chloro-3-(trifluoromethyl)phenyl]-8,11,13,14,16-pentaazatetracyclo-[8.6.0.0$^{2,7}$.0$^{11,15}$]hexadeca-1(10),2,4,6,8,12,14-heptaen-4-yl}pyridin-2-yl)acetamide;

4-(quinolin-3yl)-16-[3-(trifluoromethyl)phenyl]-8,11,13,14,16-pentaazatetracyclo-[8.6.0.0$^{2,7}$.0$^{11,15}$]hexadeca-1(10),2,4,6,8,12,14-heptaene;

16-[3,5-(trifluoromethyl)phenyl]-4-(quinolin-3yl)-8,11,13,14,16-pentaazatetracyclo-[8.6.0.0$^{2,7}$.0$^{11,15}$]hexadeca-1(10),2,4,6,8,12,14-heptaene;

16-[3-fluoro-5-(trifluoromethyl)phenyl]-4-(quinolin-3yl)-8,11,13,14,16-pentaazatetracyclo-[8.6.0.0$^{2,7}$.0$^{11,15}$]hexadeca-1(10),2,4,6,8,12,14-heptaene;

16-[2-fluoro-5-(trifluoromethyl)phenyl]-4-(quinolin-3yl)-8,11,13,14,16-pentaazatetracyclo-[8.6.0.0$^{2,7}$.0$^{11,15}$]hexadeca-1(10),2,4,6,8,12,14-heptaene;

4-(quinolin-3yl)-16-[4-(trifluoromethyl)phenyl]-8,11,13,14,16-pentaazatetracyclo-[8.6.0.0$^{2,7}$.0$^{11,15}$]hexadeca-1(10),2,4,6,8,12,14-heptaene;

EXAMPLE 3

Preparation of 2-amino-N-(5-{16-[3-(trifluoromethyl)phenyl]-8,11,13,14,16-pentaazatetracyclo-[8.6.0.0$^{2,7}$.0$^{11,15}$]hexadeca-1(10),2,4,6,8,12,14-heptaen-4-yl}pyridin-2-yl)acetamide;

To a mixture of 2-amino-5-bromopyridine (4 g, 22.86 mmol) and boc-glycine (4 g, 22.86 mmol) in DCM (200 ml)

was added EDC (4.4 g, 22.86 mmol) and HOBt (3.5 g, 22.86 mmol), the reaction was stirred and heated at 40° C. for 18 hours. The reaction was cooled and was washed with 0.25N HCl (100 ml), followed by washing with saturated NaHCO$_3$ (100 ml). The organic layer was further washed with brine and dried over sodium sulfate then evaporated under reduced pressure to give tert-butyl 2-(5-bromopyridin-2-ylamino)-2-oxoethylcarbamate 1.4 g.

A mixture of above amide (660 mg, 2 mmol), 4,4,4',4',5,5,5',5'-octamethyl-2,2'-bi(1,3,2-dioxaborolane) (1 g, 4 mmol), KOAc (1 g, 10 mmol) and (dppf)$_2$PdCl$_2$ (100 mg) in dioxane (20 ml) was heated at 110° C. for 2 hours under nitrogen. To above cooled reaction was added compound 10 (432 mg, 1 mmol), bis(triphenylphosphine)palladium(II) chloride (85 mg), 2N Na$_2$CO$_3$ (1.3 ml) and dioxane (15 ml), the reaction was heated to 110° C. for 10 hours. The reaction mixture was taken up in dichloromethane (50 ml), washed with water (30 ml), and brine (30 ml), then dried over sodium sulfate, the solid was filtered off, the filtrate was concentrated under reduced pressure and the residue was purified by prep TLC to give boc-protected titled compound (110 mg) which was mixed and stirred with 4N HCl dioxane (10 ml) for 1 hour. The reaction was then basified with Na$_2$CO$_3$ and extracted with ethyl acetate (25 ml) twice, washed with brine (30 ml), then dried over sodium sulfate, the solid was filtered off, the filtrate was concentrated under reduced pressure and the residue was purified by prep TLC to give the titled product (58 mg).

The following compound examples were prepared analogously according to the methods described in Examples 3 by using different anilines and different boronic acids.

N-[2-(morpholin-4-yl)ethyl]-5-{16-[3-(trifluoromethyl)phenyl]-8,11,13,14,16-pentaazatetra-cyclo[8.6.0.0$^{2,7}$.0$^{11,15}$]hexadeca-1(10),2,4,6,8,12,14-heptaen-4-yl}pyridin-2-amine;

2-(4-methylpiperazin-1-yl)-N-(5-{16-[3-(trifluoromethyl)phenyl]-8,11,13,14,16-pentaazatetra-cyclo[8.6.0.0$^{2,7}$.0$^{11,15}$]hexadeca-1(10),2,4,6,8,12,14-heptaen-4-yl}pyridin-2-yl)acetamide;

2-(dimethylamino)-N-(5-{16-[3-(trifluoromethyl)phenyl]-8,11,13,14,16-pentaazatetracyclo-[8.6.0.0$^{2,7}$.0$^{11,15}$]hexadeca-1(10),2,4,6,8,12,14-heptaen-4-yl}pyridin-2-yl)acetamide;

2-(morpholin-4-yl)-N-(5-{16-[3-(trifluoromethyl)phenyl]-8,11,13,14,16-pentaazatetracyclo-[8.6.0.0$^{2,7}$.0$^{11,15}$]hexadeca-1(10),2,4,6,8,12,14-heptaen-4-yl}pyridin-2-yl)acetamide;

2-(methylamino)-N-(5-{16-[3-(trifluoromethyl)phenyl]-8,11,13,14,16-pentaazatetracyclo-[8.6.0.0$^{2,7}$.0$^{11,15}$]hexadeca-1(10),2,4,6,8,12,14-heptaen-4-yl}pyridin-2-yl)acetamide;

2-amino-N-(5-{16-[4-chloro-3-(trifluoromethyl)phenyl]-8,11,13,14,16-pentaazatetracyclo-[8.6.0.0$^{2,7}$.0$^{11,15}$]hexadeca-1(10),2,4,6,8,12,14-heptaen-4-yl}pyridin-2-yl)acetamide;

N-(5-{16-[4-chloro-3-(trifluoromethyl)phenyl]-8,11,13,14,16-pentaazatetracyclo[8.6.0.0$^{2,7}$.0$^{11,15}$]-hexadeca-1(10),2,4,6,8,12,14-heptaen-4-yl}pyridin-2-yl)-2-(dimethylamino)acetamide;

N-(5-{16-[4-chloro-3-(trifluoromethyl)phenyl]-8,11,13,14,16-pentaazatetracyclo[8.6.0.0$^{2,7}$.0$^{11,15}$]-hexadeca-1(10),2,4,6,8,12,14-heptaen-4-yl}pyridin-2-yl)-2-(4-methylpiperazin-1-yl)acetamide;

N-(5-{16-[4-chloro-3-(trifluoromethyl)phenyl]-8,11,13,14,16-pentaazatetracyclo[8.6.0.0$^{2,7}$.0$^{11,15}$]-hexadeca-1(10),2,4,6,8,12,14-heptaen-4-yl}pyridin-2-yl)-2-(morpholin-4-yl)acetamide;

N-(5-{16-[4-chloro-3-(trifluoromethyl)phenyl]-8,11,13,14,16-pentaazatetracyclo[8.6.0.0$^{2,7}$.0$^{11,15}$]-hexadeca-1(10),2,4,6,8,12,14-heptaen-4-yl}pyridin-2-yl)-2-(4-oxopiperidin-1-yl)acetamide;

N-(5-{16-[4-chloro-3-(trifluoromethyl)phenyl]-8,11,13,14,16-pentaazatetracyclo[8.6.0.0$^{2,7}$.0$^{11,15}$]-hexadeca-1(10),2,4,6,8,12,14-heptaen-4-yl}pyridin-2-yl)-2-(4-hydroxypiperidin-1-yl)acetamide;

N-(5-{16-[4-chloro-3-(trifluoromethyl)phenyl]-8,11,13,14,16-pentaazatetracyclo[8.6.0.0$^{2,7}$.0$^{11,15}$]-hexadeca-1(10),2,4,6,8,12,14-heptaen-4-yl}pyridin-2-yl)-2-(pyrrolidin-1-yl)acetamide;

5-{16-[4-chloro-3-(trifluoromethyl)phenyl]-8,11,13,14,16-pentaazatetracyclo[8.6.0.0$^{2,7}$.0$^{11,15}$]-hexadeca-1(10),2,4,6,8,12,14-heptaen-4-yl}-N-[2-(pyrrolidin-1-yl)ethyl]pyridin-2-amine;

5-{16-[4-chloro-3-(trifluoromethyl)phenyl]-8,11,13,14,16-pentaazatetracyclo[8.6.0.0$^{2,7}$.0$^{11,15}$]-hexadeca-1(10),2,4,6,8,12,14-heptaen-4-yl}-N-[2-(morpholin-4-yl)ethyl]pyridin-2-amine;

5-{16-[4-chloro-3-(trifluoromethyl)phenyl]-8,11,13,14,16-pentaazatetracyclo[8.6.0.0$^{2,7}$.0$^{11,15}$]-hexadeca-1(10),2,4,6,8,12,14-heptaen-4-yl}-N-(2-methoxyethyl)pyridin-2-amine;

methyl({2-[(5-{16-[3-(trifluoromethyl)phenyl]-8,11,13,14,16-pentaazatetracyclo-[8.6.0.0$^{2,7}$.0$^{11,15}$]-hexadeca-1(10),2(7),3,5,8,12,14-heptaen-4-yl}-pyridin-2-yl)amino]ethyl})amine;

dimethyl({2-[(5-{16-[3-(trifluoromethyl)phenyl]-8,11,13,14,16-pentaazatetracyclo-[8.6.0.0$^{2,7}$.0$^{11,15}$]-hexadeca-1(10),2,4,6,8,12,14-heptaen-4-yl}pyridin-2-yl)amino]ethyl})amine;

2-(pyrrolidin-1-yl)-N-(5-{16-[3-(trifluoromethyl)phenyl]-8,11,13,14,16-pentaazatetracyclo-[8.6.0.0$^{2,7}$.0$^{11,15}$]-hexadeca-1(10),2,4,6,8,12,14-heptaen-4-yl}pyridin-2-yl)acetamide;

N-[2-(pyrrolidin-1-yl)ethyl]-5-{16-[3-(trifluoromethyl)phenyl]-8,11,13,14,16-pentaazatetracyclo-[8.6.0.0$^{2,7}$.0$^{11,15}$]-hexadeca-1(10),2,4,6,8,12,14-heptaen-4-yl}pyridin-2-amine;

2-[(5-{16-[3-(trifluoromethyl)phenyl]-8,11,13,14,16-pentaazatetracyclo-[8.6.0.0$^{2,7}$.0$^{11,15}$]-hexadeca-1(10),2,4,6,8,12,14-heptaen-4-yl}pyridin-2-yl-amino]ethan-1-ol;

N-(2-methoxyethyl)-5-{16-[3-(trifluoromethyl)phenyl]-8,11,13,14,16-pentaazatetracyclo-[8.6.0.0$^{2,7}$.0$^{11,15}$]-hexadeca-1(10),2,4,6,8,12,14-heptaen-4-yl}pyridin-2-amine;

{2-[(5-{16-[4-chloro-3-(trifluoromethyl)phenyl]-8,11,13,14,16-pentaazatetracyclo-[8.6.0.0$^{2,7}$.0$^{11,15}$]-hexadeca-1(10),2,4,6,8,12,14-heptaen-4-yl}pyridin-2-yl)amino]ethyl}-dimethylamine;

5-{16-[4-(trifluoromethyl)phenyl]-8,11,13,14,16-pentaazatetracyclo-[8.6.0.0$^{2,7}$.0$^{11,15}$]-hexadeca-1(10),2,4,6,8,12,14-heptaen-4-yl}-N-[2-(4-methylpiperazin-1-yl)ethyl]-pyridin-2-amine;

2-[(5-{16-[4-chloro-3-(trifluoromethyl)phenyl]-8,11,13,14,16-pentaazatetracyclo-[8.6.0.0$^{2,7}$.0$^{11,15}$]-hexadeca-1(10),2,4,6,8,12,14-heptaen-4-yl}pyridin-2-yl)amino]ethanol;

EXAMPLE 4

Preparation of 4-(pyridin-3-yl)-16-[3-(trifluoromethyl)phenyl]-8,11,14,16-tetraazatetracyclo-[8.6.0.0$^{2,7}$.0$^{11,15}$]-hexadeca-1(10),2,4,6,8,12,14-heptaene To the suspension of compound 8 (200 mg) in ethanol (10 ml) was added ammonium hydroxide (0.5 ml), the resulting mixture was heated at 90° C. in a sealed tube for 10 hours. After cooled to room temperature, the reaction solution was concentrated under reduced pressure, then the residue was taken up in dichloromethane (20 ml) and was washed sequentially by water (20 ml), and brine (20 ml). The organic phase was dried over sodium sulfate, the solid was filtered off and the filtrate was concentrated and further purified on silica gel column to give 8-bromo-1-(3-(trifluromethyl) phenyl)-1H-imidazo[4,5-c]quinolin-2-amine (55 mg) which was mixed with 2-bromomethyl-1,3-dioxolane (100 mg) in toluene (1 mg) with a drop of TFA. The reaction was heated at 110° C. in a sealed tube for 16 hours and evaporated to be further purified on silica gel column to give 4-bromo-16-[3-(trifluoromethyl)phenyl]-8,11,14,16-tetraazatetracyclo[8.6.0.0$^{2,7}$.0$^{11,15}$]hexadeca-1(10),2,4,6,-8,12,14-heptaene which was similarly reacted with pyridine boronic acid as described above via Suzuki reaction to give the titled product 22 mg, (M+1) 430.

Examples of Formulation:

The following are the examples of the formulations and these are purely illustrative and in no way to be interpreted as restrictive.

Formulation Example 1:

Each capsule contains:

| | |
|---|---|
| One Compound from above compounds | 100.0 mg |
| Corn starch | 23.0 mg |
| Calcium carboxymethyl cellulose | 22.5 mg |
| Hydroxypropylmethyl cellulose | 3.0 mg |
| Magnesium stearate | 1.5 mg |
| | 150.0 mg |

Formulation Example 2:

A solution contains:

| | |
|---|---|
| One Compound from above compounds | 1 to 10 g |
| Acetic acid or sodium hydroxide | 0.5 to 1 g |
| Ethyl p-hydroxybenzoate | 0.1 g |
| Purified water | 88.9 to 98.4 g |
| | 100.0 g |

Formulation Example 3:

A powder for admixing with feedstuff contains:

| | |
|---|---|
| One Compound from above compounds | 1 to 10 g |
| Corn starch | 98.5 to 89.5 g |
| Light anhydrous silicic acid | 0.5 g |
| | 100.0 g |

What is claimed is:

1. A compound of formula I

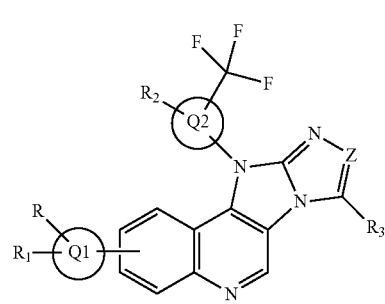

Formula I wherein

Q1 and Q2 are independently selected from an aryl, a 5-6 membered heterocyclyl or a 9-11 membered bicycloheterocyclyl;

Z is N or C—R;

R and R$_1$, when present, are independently selected from H, halogen, halogenC$_1$-C$_6$alkyl, —C$_1$-C$_6$alkyl, —OR$_7$, —NR$_7$R$_8$, or are not present;

wherein when R and R$_1$ are not present Q1 is a halogen;

R$_2$ and R$_3$ are independently selected from H, halogen, —OH, —C$_1$-C$_6$alkyl, —C$_1$-C$_6$alkoxyl, —C$_1$-C$_6$alkenyl or —C$_1$-C$_6$alkynyl;

R$_7$ and R$_8$ are independently selected from H, halogen, —C$_1$-C$_6$alkyl, —C$_1$-C$_6$alkylOH, —C$_1$-C$_6$alkoxyl, —C$_1$-C$_6$alkylNR$_4$R$_5$, —C(═O)C$_1$-C$_6$alkyl, —C(═O)C$_1$-C$_6$alkyl-R$_4$R$_5$, —C(═O)C$_1$-C$_6$alkylOH, —C(═O)C$_1$-C$_6$alkoxyl, —C(═O)C$_1$-C$_6$alkylNR$_4$R$_5$, —C(═O)OC$_1$-C$_6$alkyl, —C(═O)OC$_1$-C$_6$alkylOH, —C(═O)OC$_1$-C$_6$alkoxyl, —C(═O)OC$_1$-C$_6$alkylNR$_4$R$_5$, —C(═O)NR$_4$C$_1$-C$_6$alkyl, —C(═O)NR$_4$C$_1$-C$_6$al-ky-lOH, —C(═O)NR$_4$C$_1$-C$_6$alkoxyl, —C(═O)NR$_4$C$_1$-C$_6$alkylNR$_4$R$_5$;

R$_4$ and R$_5$ are independently selected from H, halogen, halogenC$_1$-C$_6$alkyl, —C$_1$-C$_6$alkyl, —OH, —C$_1$-C$_6$alkoxyl, cycloalkyl; or both R$_4$ and R$_5$ can be combined together to form a 3-8 membered saturated or unsaturated ring that can be aliphatic cyclyl or heterocyclyl;

or a pharmaceutically acceptable salt thereof.

2. The compound of claim 1, wherein

Q1 is independently selected from pyridinyl, pyrimidinyl, quinolinyl or quinazolinyl and Q2 is phenyl;

Z is N or C—R;

R and R$_1$ are independently selected from H, halogen, halogenC$_1$-C$_6$alkyl, C$_1$-C$_6$alkyl, —OR$_7$, or —NR$_7$R$_8$;

R$_2$ and R$_3$ are independently selected from H, —OH, —C$_1$-C$_6$alkyl, —C$_1$-C$_6$alkoxyl, —C$_1$-C$_6$alkenyl or —C$_1$-C$_6$alkynyl;

R$_4$ and R$_5$ are independently selected from H, halogen, halogenC$_1$-C$_6$alkyl, —C$_1$-C$_6$alkyl, —OH, —C$_1$-C$_6$alkoxyl, cycloalkyl; or both R$_4$ and R$_5$ can be combined together to form a 3-8 membered saturated or unsaturated ring that can be aliphatic cyclyl or heterocyclyl;

R$_7$ and R$_8$ are independently selected from H, halogen, —C$_1$-C$_6$alkyl, —C(═O)—C$_1$-C$_6$alkyl-R$_4$R$_5$, —C$_1$-C$_6$alkylOH, —C$_1$-C$_6$alkoxyl, —C$_1$-C$_6$alkylNR$_4$R$_5$, —C(═O)—C$_1$-C$_6$alkyl, —C(═O)—C$_1$-C$_6$alkylOH, —C(═O)—C$_1$-C$_6$alkoxyl, —C(═O)—C$_1$-C$_6$alkylNR$_4$R$_5$, —C(═O)OC$_1$-C$_6$alkyl, —C(═O)OC$_1$-C$_6$alkylOH, —C(═O)OC$_1$-C$_6$alkoxyl, —C(═O)OC$_1$-C$_6$alkylNR$_4$R$_5$, —C(═O)NR$_4$C$_1$-C$_6$alkyl, —C(═O)NR$_4$C$_1$-C$_6$alkylOH, —C(═O)—NR$_4$C$_1$-

$C_6$alkoxyl, —C(═O)NR$_4$C$_1$-C$_6$alkylNR$_4$R$_5$; preferably are independently selected from H, —C(═O)C$_1$-C$_6$alkyl, —C$_1$-C$_6$alkylNR$_4$R$_5$ or —C(═O)C$_1$-C$_6$alkylNR$_4$R$_5$;

or a pharmaceutically acceptable salt thereof.

3. The compound of claim 1, represented by formula II

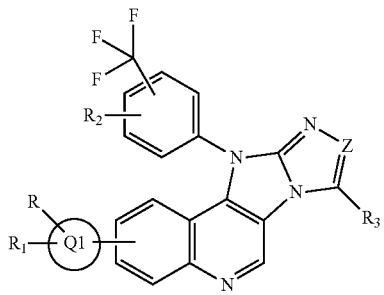

Formula II wherein

Q1 is independently selected from pyridinyl, pyrimidinyl, quinolinyl or quinazolinyl;

Q1 is a halogen selected from Br and I when R and R$_1$ are not present;

Z is N or C—R;

R and R$_1$ are independently selected from H, halogen, halogenC$_1$-C$_6$alkyl, —C$_1$-C$_6$alkyl, —OR$_7$, or —NR$_7$R$_8$;

R$_2$ and R$_3$ are independently selected from H, —OH, —C$_1$-C$_6$alkyl, —C$_1$-C$_6$alkoxyl, —C$_1$-C$_6$alkenyl or —C$_1$-C$_6$alkynyl;

R$_4$ and R$_5$ are independently selected from H, halogenC$_1$-C$_6$alkyl, —C$_1$-C$_6$alkyl or both combined together to form a saturated aliphatic cyclyl or heterocyclyl ring;

R$_7$ and R$_8$ are independently selected from H, halogen, —C$_1$-C$_6$alkyl, —C$_1$-C$_6$alkylOH, —C$_1$-C$_6$alkoxyl, —C$_1$-C$_6$alkylNR$_4$R$_5$, —C(═O)C$_1$-C$_6$alkyl, —C(═O)C$_1$-C$_6$alkyl-R$_4$R$_5$, —C(═O)OC$_1$-C$_6$alkylOH, —C(═O)C$_1$-C$_6$alkoxyl, —C(═O)C$_1$-C$_6$alkylNR$_4$R$_5$, —C(═O)OC$_1$-C$_6$alkyl, —C(═O)OC$_1$-C$_6$alkylOH, —C(═O)OC$_1$-C$_6$alkoxyl, —C(═O)OC$_1$-C$_6$alkylNR$_4$R$_5$, —C(═O)NR$_4$C$_1$-C$_6$alkyl, —C(═O)NR$_4$C$_1$-C$_6$alkylOH, —C(═O)—NR$_4$C$_1$-C$_6$alkoxyl, —C(═O)NR$_4$C$_1$-C$_6$alkylNR$_4$R$_5$;

or a pharmaceutically acceptable salt thereof.

4. The compound of claim 1, wherein the compound is selected from the group consisting of:

4-bromo-16-[3-(trifluoromethyl)phenyl]-8,11,13,14,16-pentaazatetracyclo[8.6.0.0$^{2,7}$.0$^{11,15}$]-hexadeca-1(10),2,4,6,8,12,14-heptaene;

16-(3-(trifluoromethyl)phenyl)-4-(pyridin-3-yl)-8,11,13,14,16-pentaazatetracyclo-[8.6.0.0$^{2,7}$.0$^{11,15}$]hexadeca-1(10),2,4,6,8,12,14-heptaene;

12-ethyl-16-[4-fluoro-3-(trifluoromethyl)phenyl]-4-(pyridin-3-yl)-8,11,13,14,16-pentaazatetra-cyclo-[8.6.0.0$^{2,7}$.0$^{11,15}$]hexadeca-1(10),2,4,6,8,12,14-heptaene 4-bromo-16-[4-chloro-3-(trifluoromethyl)phenyl]-8,11,13,14,16-pentaazatetracyclo-[8.6.0.0$^{2,7}$.0$^{11,15}$]hexadeca-1(10),2,4,6,8,12,14-heptaene;

16-[3,5-bis(trifluoromethyl)phenyl]-4-bromo-8,11,13,14,16-pentaazatetracyclo[8.6.0.0$^{2,7}$.0$^{11,15}$]-hexadeca-1(10),2,4,6,8,12,14-heptaene;

4-bromo-16-[3-fluoro-5-(trifluoromethyl)phenyl]-8,11,13,14,16-pentaazatetracyclo-[8.6.0.0$^{2,7}$.0$^{11,15}$]hexadeca-1(10),2,4,6,8,12,14-heptaene;

4-bromo-16-[2-fluoro-5-(trifluoromethyl)phenyl]-8,11,13,14,16-pentaazatetracyclo-[8.6.0.0$^{2,7}$.0$^{11,15}$]hexadeca-1(10),2,4,6,8,12,14-heptaene;

4-bromo-16-[4-fluoro-3-(trifluoromethyl)phenyl]-8,11,13,14,16-pentaazatetracyclo-[8.6.0.0$^{2,7}$.0$^{11,15}$]hexadeca-1(10),2,4,6,8,12,14-heptaene;

12-ethyl-16-[4-fluoro-3-(trifluoromethyl)phenyl]-4-(quinolin-3-yl)-8,11,13,14,16-pentaazate-tracyclo[8.6.0.0$^{2,7}$.0$^{11,15}$]hexadeca-1(10),2,4,6,8,12,14-heptaene;

16-[4-chloro-3-(trifluoromethyl)phenyl]-4-(quinolin-3-yl)-8,11,13,14,16-pentaazatetracyclo-[8.6.0.0$^{2,7}$.0$^{11,15}$]hexadeca-1(10),2,4,6,8,12,14-heptaene;

16-[4-chloro-3-(trifluoromethyl)phenyl]-4-(pyridin-3-yl)-8,11,13,14,16-pentaazatetracyclo-[8.6.0.0$^{2,7}$.0$^{11,15}$]hexadeca-1(10),2,4,6,8,12,14-heptaene;

5-{16-[4-chloro-3-(trifluoromethyl)phenyl]-8,11,13,14,16-pentaazatetracyclo[8.6.0.0$^{2,7}$.0$^{11,15}$]-hexadeca-1(10),2,4,6,8,12,14-heptaen-4-yl}pyridin-2-amine;

16-[4-chloro-3-(trifluoromethyl)phenyl]-4-(3-fluorophenyl)-8,11,13,14,16-pentaazatetracyclo-[8.6.0.0$^{2,7}$.0$^{11,15}$]hexadeca-1(10),2,4,6,8,12,14-heptaene;

16-[4-chloro-3-(trifluoromethyl)phenyl]-4-(3,4-difluorophenyl)-8,11,13,14,16-pentaazatetra-cyclo-[8.6.0.0$^{2,7}$.0$^{11,15}$]hexadeca-1(10),2,4,6,8,12,14-heptaene;

16-[4-chloro-3-(trifluoromethyl)phenyl]-4-(2-fluorophenyl)-8,11,13,14,16-pentaazatetracyclo-[8.6.0.0$^{2,7}$.0$^{11,15}$]hexadeca-1(10),2,4,6,8,12,14-heptaene;

N-(5-{16-[4-chloro-3-(trifluoromethyl)phenyl]-8,11,13,14,16-pentaazatetracyclo-[8.6.0.0$^{2,7}$.0$^{11,15}$]hexadeca-1(10),2,4,6,8,12,14-heptaen-4-yl}pyridin-2-yl)acetamide;

4-(quinolin-3-yl)-16-[3-(trifluoromethyl)phenyl]-8,11,13,14,16pentaazatetracyclo-[8.6.0.0$^{2,7}$.0$^{11,15}$]hexadeca-1(10),2,4,6,8,12,14-heptaene;

16-[3,5-bis(trifluoromethyl)phenyl]-4-(quinolin-3-yl)-8,11,13,14,16-pentaazatetracyclo-[8.6.0.0$^{2,7}$.0$^{11,15}$]hexadeca-1(10),2,4,6,8,12,14-heptaene;

16-[3-fluoro-5-(trifluoromethyl)phenyl]-4-(quinolin-3-yl)-8,11,13,14,16-pentaazatetracyclo-[8.6.0.0$^{2,7}$.0$^{11,15}$]hexadeca-1(10),2,4,6,8,12,14-heptaene;

16-[2-fluoro-5-(trifluoromethyl)phenyl]-4-(quinolin-3-yl)-8,11,13,14,16-pentaazatetracyclo-[8.6.0.0$^{2,7}$.0$^{11,15}$]hexadeca-1(10),2,4,6,8,12,14-heptaene;

4-(quinolin-3-yl)-16-[4-(trifluoromethyl)phenyl]-8,11,13,14,16-pentaazatetracyclo-[8.6.0.0$^{2,7}$.0$^{11,15}$]hexadeca-1(10),2,4,6,8,12,14-heptaene;

2-amino-N-(5-{16-[3-(trifluoromethyl)phenyl]-8,11,13,14,16-pentaazatetracyclo-[8.6.0.0$^{2,7}$.0$^{11,15}$]hexadeca-1(10),2,4,6,8,12,14-heptaen-4-yl}pyridin-2-yl)acetamide;

N-[2-(morpholin-4-yl)ethyl]-5-{16-[3-(trifluoromethyl)phenyl]-8,11,13,14,16-pentaazatetra-cyclo[8.6.0.0$^{2,7}$.0$^{11,15}$]hexadeca-1(10),2,4,6,8,12,14-heptaen-4-yl}pyridin-2-amine;

2-(4-methylpiperazin-1-yl)-N-(5-{16-[3-(trifluoromethyl)phenyl]-8,11,13,14,16-pentaazatetra-cyclo[8.6.0.0$^{2,7}$.0$^{11,15}$]hexadeca-1(10),2,4,6,8,12,14-heptaen-4-yl}pyridin-2-yl)acetamide;

2-(dimethylamino)-N-(5-{16-[3-(trifluoromethyl)phenyl]-8,11,13,14,16-pentaazatetracyclo-[8.6.0.0$^{2,7}$.0$^{11,15}$]hexadeca-1(10),2,4,6,8,12,14-heptaen-4-yl}pyridin-2-yl)acetamide;

2-(morpholin-4-yl)-N-(5-{16-[3-(trifluoromethyl)phenyl]-8,11,13,14,16-pentaazatetracyclo-[8.6.0.0$^{2,7}$.0$^{11,15}$]hexadeca-1(10),2,4,6,8,12,14-heptaen-4-yl}pyridin-2-yl)acetamide;

2-(methylamino)-N-(5-{16-[3-(trifluoromethyl)phenyl]-8,11,13,14,16-pentaazatetracyclo-[8.6.0.0$^{2,7}$.0$^{11,15}$]hexadeca-1(10),2,4,6,8,12,14-heptaen-4-yl}pyridin-2-yl)acetamide;

2-amino-N-(5-{16-[4-chloro-3-(trifluoromethyl)phenyl]-8,11,13,14,16-pentaazatetracyclo-[8.6.0.0$^{2,7}$.0$^{11,15}$]hexadeca-1(10),2,4,6,8,12,14-heptaen-4-yl}pyridin-2-yl)acetamide;

N-(5-{16-[4-chloro-3-(trifluoromethyl)phenyl]-8,11,13,14,16-pentaazatetracyclo-[8.6.0.0$^{2,7}$.0$^{11,15}$]-hexadeca-1(10),2,4,6,8,12,14-heptaen-4-yl}pyridin-2-yl)-2-(dimethylamino)acetamide;

N-(5-{16-[4-chloro-3-(trifluoromethyl)phenyl]-8,11,13,14,16-pentaazatetracyclo-[8.6.0.0$^{2,7}$.0$^{11,15}$]-hexadeca-1(10),2,4,6,8,12,14-heptaen-4-yl}pyridin-2-yl)-2-(4-methylpiperazin-1-yl)acetamide;

N-(5-{16-[4-chloro-3-(trifluoromethyl)phenyl]-8,11,13,14,16-pentaazatetracyclo[8.6.0.0$^{2,7}$.0$^{11,15}$]-hexadeca-1(10),2,4,6,8,12,14-heptaen-4-yl}pyridin-2-yl)-2-(morpholin-4-yl)acetamide;

N-(5-{16-[4-chloro-3-(trifluoromethyl)phenyl]-8,11,13,14,16-pentaazatetracyclo[8.6.0.0$^{2,7}$.0$^{11,15}$]-hexadeca-1(10),2,4,6,8,12,14-heptaen-4-yl}pyridin-2-yl)-2-(4-oxopiperidin-1-yl)acetamide;

N-(5-{16-[4-chloro-3-(trifluoromethyl)phenyl]-8,11,13,14,16-pentaazatetracyclo[8.6.0.0$^{2,7}$.0$^{11,15}$]-hexadeca-1(10),2,4,6,8,12,14-heptaen-4-yl}pyridin-2-yl)-2-(4-hydroxypiperidin-1-yl)acetamide;

N-(5-{16-[4-chloro-3-(trifluoromethyl)phenyl]-8,11,13,14,16-pentaazatetracyclo[8.6.0.0$^{2,7}$.0$^{11,15}$]-hexadeca-1(10),2,4,6,8,12,14-heptaen-4-yl}pyridin-2-yl)-2-(pyrrolidin-1-yl)acetamide;

5-{16-[4-chloro-3-(trifluoromethyl)phenyl]-8,11,13,14,16-pentaazatetracyclo[8.6.0.0$^{2,7}$.0$^{11,15}$]-hexadeca-1(10),2,4,6,8,12,14-heptaen-4-yl}-N-[2-(pyrrolidin-1-yl)ethyl]pyridin-2-amine;

5-{16-[4-chloro-3-(trifluoromethyl)phenyl]-8,11,13,14,16-pentaazatetracyclo[8.6.0.0$^{2,7}$.0$^{11,15}$]-hexadeca-1(10),2,4,6,8,12,14-heptaen-4-yl}-N-[2-(morpholin-4-yl)ethyl]pyridin-2-amine;

5-{16-[4-chloro-3-(trifluoromethyl)phenyl]-8,11,13,14,16-pentaazatetracyclo[8.6.0.0$^{2,7}$.0$^{11,15}$]-hexadeca-1(10),2,4,6,8,12,14-heptaen-4-yl}-N-(2-methoxyethyl)pyridin-2-amine;

methyl({2-[(5-{16-[3-(trifluoromethyl)phenyl]-8,11,13,14,16-pentaazatetracyclo-[8.6.0.0$^{2,7}$.0$^{11,15}$]-hexadeca-1(10),2,4,6,8,12,14-heptaen-4-yl}pyridin-2-yl)amino]ethyl})amine;

dimethyl({2-[(5-{16-[3-(trifluoromethyl)phenyl]-8,11,13,14,16-pentaazatetracyclo-[8.6.0.0$^{2,7}$.0$^{11,15}$]hexadeca-1(10),2,4,6,8,12,14-heptaen-4-yl}pyridin-2-yl)amino]ethyl})amine;

2-(pyrrolidin-1-yl)-N-(5-{16-[3-(trifluoromethyl)phenyl]-8,11,13,14,16-pentaazatetracyclo-[8.6.0.0$^{2,7}$.0$^{11,15}$]hexadeca-1(10),2,4,6,8,12,14-heptaen-4-yl}pyridin-2-yl)acetamide;

N-[2-(pyrrolidin-1-yl)ethyl]-5-{16-[3-(trifluoromethyl)phenyl]-8,11,13,14,16pentaazatetracyclo-[8.6.0.0$^{2,7}$.0$^{11,15}$]hexadeca-1(10),2,4,6,8,12,14-heptaen-4-yl}pyridin-2-amine;

2-[5-{16-[3-(trifluoromethyl)phenyl]-8,11,13,14,16-pentaazatetracyclo[8.6.0.0$^{2,7}$.0$^{11,15}$]-hexadeca-1(10),2,4,6,8,12,14-heptaen-4-yl}pyridin-2-yl)amino]ethan-1-ol;

N-(2-methoxyethyl)-5-{16-[3-(trifluoromethyl)phenyl]-8,11,13,14,16-pentaazatetracyclo-[8.6.0.0$^{2,7}$.0$^{11,15}$]hexadeca-1(10),2,4,6,8,12,14heptaen-4-yl}pyridin-2-amine;

{2-[(5-{16-[4-chloro-3-(trifluoromethyl)phenyl]-8,11,13,14,16-pentaazatetracyclo[8.6.0.0$^{2,7}$.0$^{11,15}$]-hexadeca-1(10),2,4,6,8,12,14-heptaen-4-yl}pyridin-2-yl)amino]ethyl}-dimethylamine;

5-{16-[4-chloro-3-(trifluoromethyl)phenyl]-8,11,13,14,16-pentaazatetracyclo-[8.6.0.0$^{2,7}$.0$^{11,15}$]-hexadeca-1(10),2,4,6,8,12,14-heptaen-4-yl}-N-[2-(4-methylpiperazin-1-yl)ethyl]-pyridin-2-amine;

2-[(5-{16-[4-chloro-3-(trifluoromethyl)phenyl]-8,11,13,14,16-pentaazatetracyclo-[8.6.0.0$^{2,7}$.0$^{11,15}$]-hexadeca-1(10),2,4,6,8,12,14-heptaen-4-yl}pyridin-2-yl)amino]ethanol;

4-(pyridin-3-yl)-16-[3-(trifluoromethyl)phenyl]-8,11,14,16-tetraazatetracyclo-[8.6.0.0$^{2,7}$.0$^{11,15}$]-hexadeca-1(10),2,4,6,8,12,14-heptaene or a pharmaceutically acceptable salt thereof.

5. A method of producing the compound of claim 1, the method comprising the following steps:

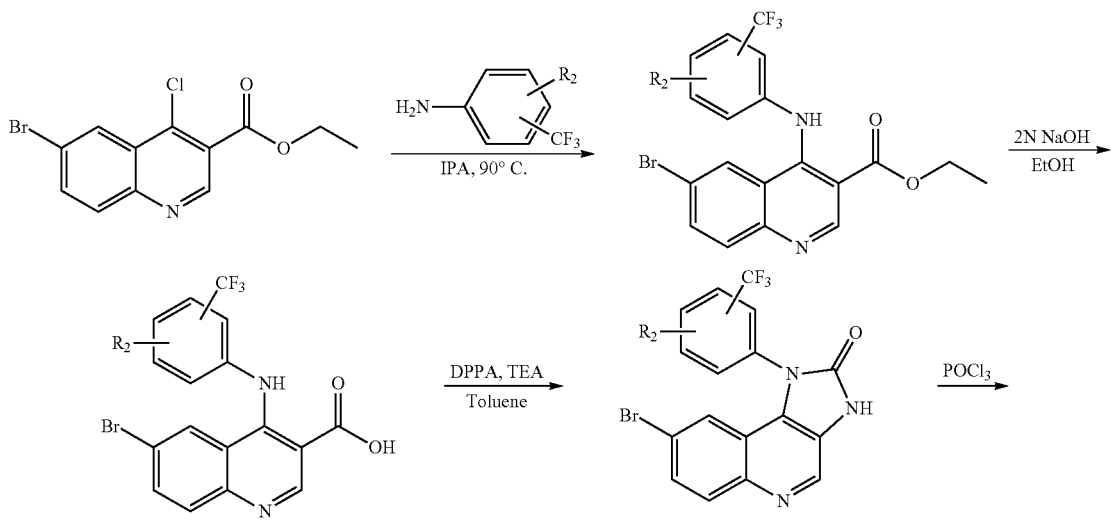

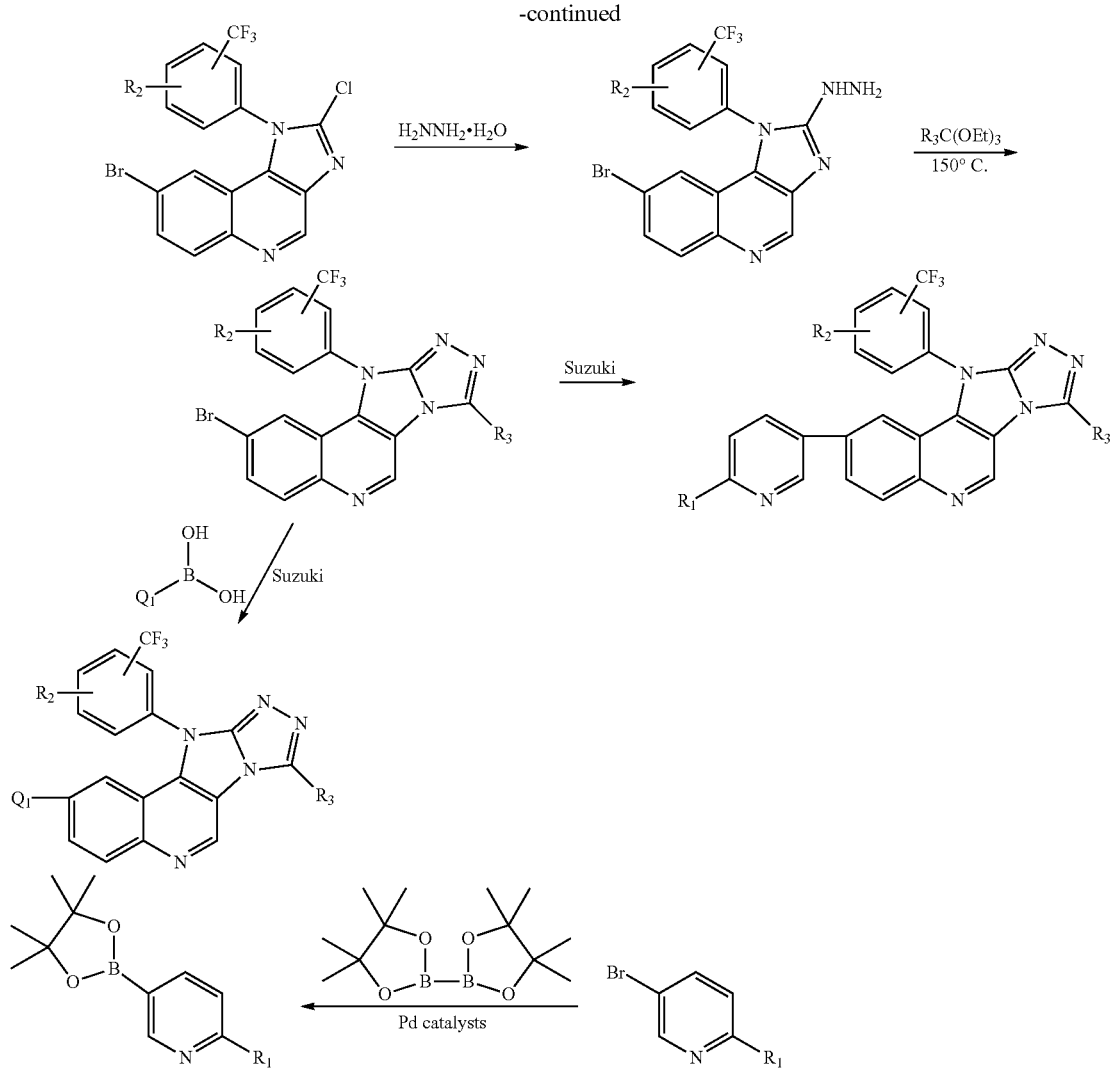

wherein

R₁ is selected from —NH₂, —NHCH₃, —N(CH₃)₂, —NHCOCH₃, —NHCO(CH₂)$_n$CH₃, —NHCO(CH₂)$_n$NH₂, —NHCO(CH₂)$_n$NHCH₃, —NHCO(CH₂)$_n$N(CH₃)₂, —NHCO(CH²)$_n$-Pyrrolidine, —NHCO(CH₂)$_n$-Piperazine, —NHCO(CH₂)$_n$-Morpholine, —NH(CH₂)$_n$NHCH₃, —NH(CH₂)$_n$N(CH₃)₂, —NH(CH₂)$_n$-Pyrrolidine, —NH(CH₂)$_n$-Piperazine, —NH(CH²)$_n$-Morpholine;

n is 1, 2, 3, or 4;

R₂ is H, halogen, or —C₁-C₆alkyl;

R₃ is H or —C₁-C₆alkyl; and

Q₁ is independently selected from pyridine, pyrimidine, quinolone, or quinazoline.

6. The compound of claim 1, wherein Q1 is a halogen Br or I.

7. The compound of claim 1, represented by the following formula:

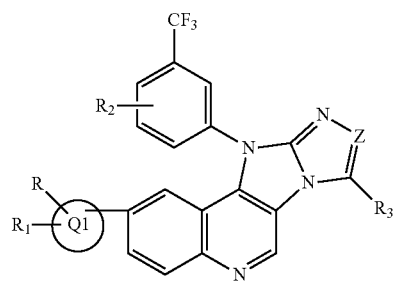

wherein

R₂, and R₃ are as defined as in any of compounds "a" through "tt" in Table A:

TABLE A

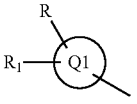

| | R | R₂ | R₃ |
|---|---|---|---|
| a | 3-pyridine | 4-F | CH₂CH₃ |
| b | 3-pyridine | 4-F | H |
| c | 3-quinoline | 4-F | H |
| d | 3-quinoline | 4-Cl | H |
| e | 3-pyridine | 4-Cl | H |
| f | 5-pyridin-2-amine | 4-Cl | H |
| g | 3-Flurophenyl | 4-Cl | H |
| h | 3,4-Diflurophenyl | 4-Cl | H |
| i | 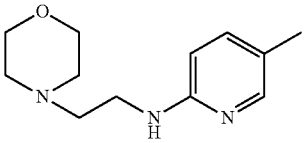 | H | H |
| j | 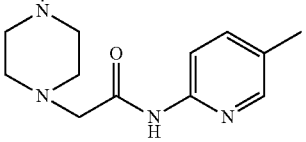 | H | H |
| k | 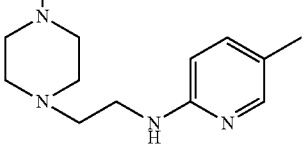 | H | H |
| l | 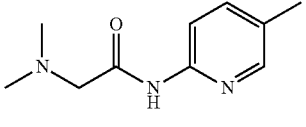 | H | H |
| m | 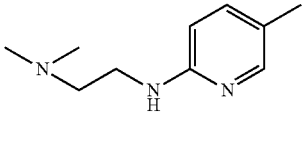 | H | H |
| n | 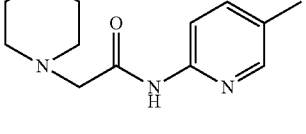 | H | H |
| o | 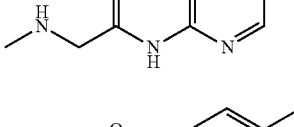 | H | H |
| p | 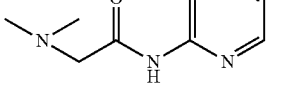 | 4-Cl | H |

TABLE A-continued

| | R | R₂ | R₃ |
|---|---|---|---|
| q | 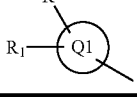 | 4-Cl | H |
| r | 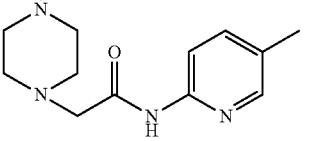 | 4-Cl | H |
| s | 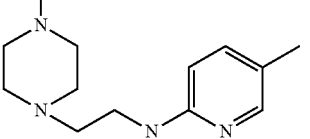 | 4-Cl | H |
| t | 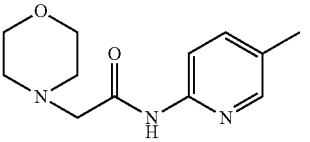 | 4-Cl | H |
| u | 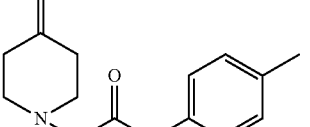 | 4-Cl | H |
| v | Br | 4-Cl | H |
| w | Br | H | H |
| x | Br | 5-CF₃ | CH₃ |
| y | 2-Flurophenyl | 4-Cl | H |
| z | N-(5-pyridin-2-yl)acetamide | 4-Cl | H |
| aa | 3-quinoline | H | H |
| bb | 3-pyridine | H | H |
| cc | 3-quinoline | 5-CF₃ | H |
| dd | 3-quinoline | 5-F | H |
| ee | 3-quinoline | 6-F | H |
| ff | 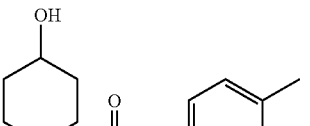 | H | H |
| gg | 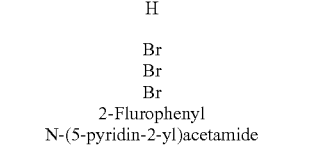 | H | H |
| hh | 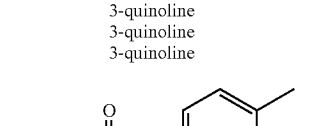 | H | H |

TABLE A-continued

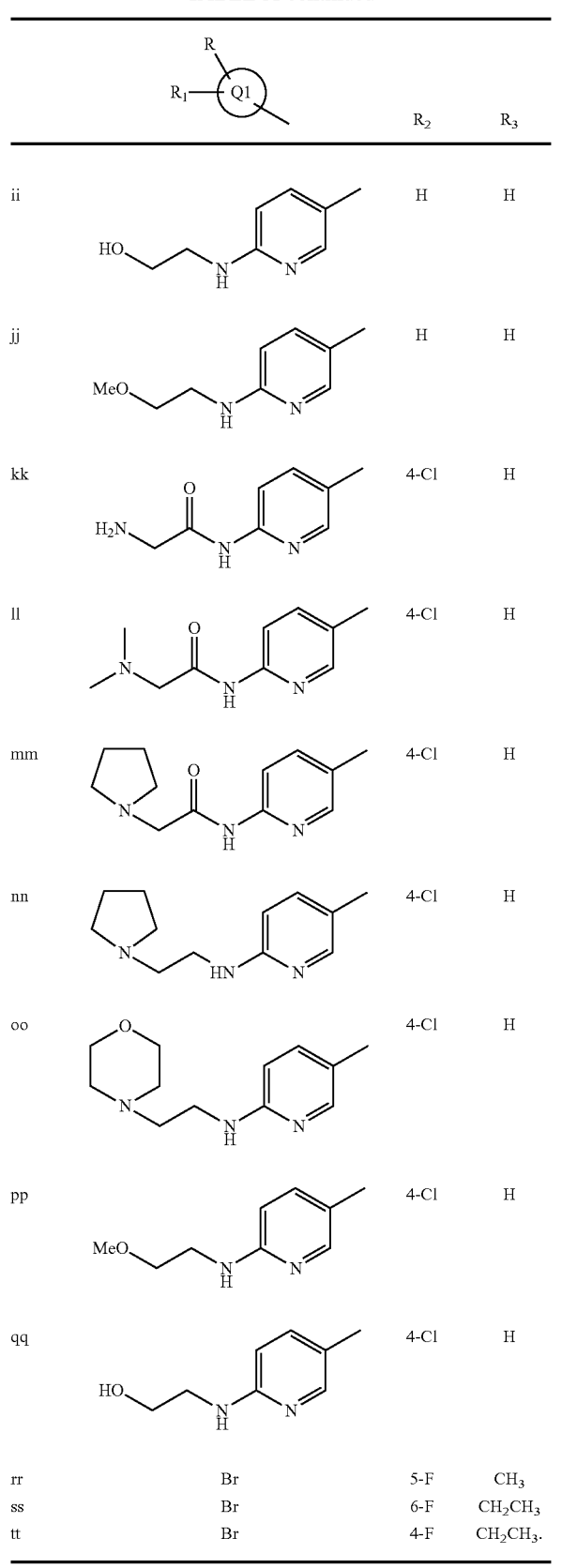

| | | R₂ | R₃ |
|---|---|---|---|
| ii | HO–CH₂CH₂–NH–(5-methylpyridin-2-yl) | H | H |
| jj | MeO–CH₂CH₂–NH–(5-methylpyridin-2-yl) | H | H |
| kk | H₂N–CH₂–C(=O)–NH–(5-methylpyridin-2-yl) | 4-Cl | H |
| ll | Me₂N–CH₂–C(=O)–NH–(5-methylpyridin-2-yl) | 4-Cl | H |
| mm | pyrrolidinyl–CH₂–C(=O)–NH–(5-methylpyridin-2-yl) | 4-Cl | H |
| nn | pyrrolidinyl–CH₂CH₂–NH–(5-methylpyridin-2-yl) | 4-Cl | H |
| oo | morpholinyl–CH₂CH₂–NH–(5-methylpyridin-2-yl) | 4-Cl | H |
| pp | MeO–CH₂CH₂–NH–(5-methylpyridin-2-yl) | 4-Cl | H |
| qq | HO–CH₂CH₂–NH–(5-methylpyridin-2-yl) | 4-Cl | H |
| rr | Br | 5-F | CH₃ |
| ss | Br | 6-F | CH₂CH₃ |
| tt | Br | 4-F | CH₂CH₃ |

8. The compound of claim 1, represented by the following formula:

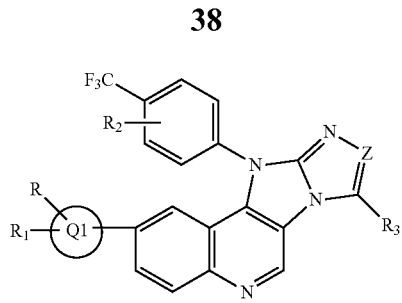

wherein

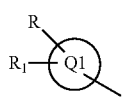

is 3-quinoline and wherein R₂ and R₃ are H.

9. The compound of claim 1, represented by the following formula

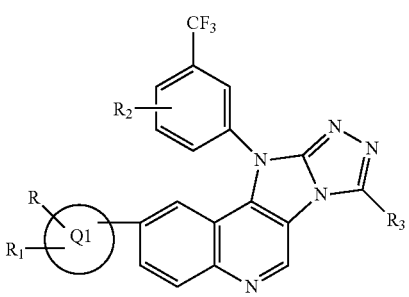

wherein
Q1 is a 9-11 membered bicycloheterocyclyl;
R and R₁ are independently selected from H, halogen, halogenC₁-C₆alkyl, —C₁-C₆alkyl, —OR₇, —NR₇R₈, or are not present;
wherein when R and R₁ are not present Q1 is a halogen;
R₂ is selected from H, halogen, —OH, —C₁-C₆alkyl, —C₁-C₆alkoxyl, —C₁-C₆alkenyl or —C₁-C₆alkynyl;
R₇ and R₈ are independently selected from H, halogen, —C₁-C₆alkyl, —C₁-C₆alkylOH, —C₁-C₆alkoxyl, —C₁-C₆alkylNR₄R₅, —C(=O)C₁-C₆alkyl, —C(=O)C₁-C₆alkyl-R₄R₅, —C(=O)C₁-C₆alkylOH, —C(=O)C₁-C₆alkoxyl, —C(=O)C₁-C₆alkylNR₄R₅, —C(=O)OC₁-C₆alkyl, —C(=O)OC₁-C₆alkylOH, —C(=O)OC₁-C₆alkoxyl, —C(=O)OC₁-C₆alkylNR₄R₅, —C(=O)NR₄C₁-C₆alkyl, —C(=O)NR₄C₁-C₆al-kylOH, —C(=O)NR₄C₁-C₆alkoxyl, —C(=O)NR₄C₁-C₆alkylNR₄R₅; and
R₄ and R₅ are independently selected from H, halogen, halogenC₁-C₆alkyl, —C₁-C₆alkyl, —OH, —C₁-C₆alkoxyl, cycloalkyl; or both R₄ and R₅ can be combined together to form a 3-8 membered saturated or unsaturated ring that can be aliphatic cyclyl or heterocyclyl.

10. The compound of claim 9, wherein R is H, R₁ is H, and R₂ is halogen.

11. The compound of claim 1, wherein the compound is selected from:
12-ethyl-16-[4-fluoro-3-(trifluoromethyl)phenyl]-4-(quinolin-3-yl)-8,11,13,14,16-pentaazate-tracyclo[8.6.0.0²,⁷.0¹¹,¹⁵]hexadeca-1(10),2,4,6,8,12,14-heptaene;

16-[4-fluoro-3-(trifluoromethyl)phenyl]-4-(quinolin-3-yl)-8,11,13,14,16-pentaazatetracyclo-[8.6.0.0$^{2,7}$.0$^{11,15}$]hexadeca-1(10),2,4,6,8,12,14-heptaene;

16-[4-fluoro-3-(trifluoromethyl)phenyl]-4-(pyridin-3-yl)-8,11,13,14,16-pentaazatetracyclo-[8.6.0.0$^{2,7}$.0$^{11,15}$]hexadeca-1(10),2,4,6,8,12,14-heptaene;

5-{16-[4-chloro-3-(trifluoromethyl)phenyl]-8,11,13,14,16-pentaazatetracyclo-[8.6.0.0$^{2,7}$.0$^{11,15}$]hexadeca-1(10),2,4,6,8,12,14-heptaen-4-yl}pyridin-2-amine;

16-[4-chloro-3-(trifluoromethyl)phenyl]-4-(3-fluorophenyl)-8,11,13,14,16-pentaazatetracyclo-[8.6.0.0$^{2,7}$.0$^{11,15}$]hexadeca-1(10),2,4,6,8,12,14-heptaene;

16-[4-chloro-3-(trifluoromethyl)phenyl]-4-(3,4-difluorophenyl)-8,11,13,14,16-pentaazatetra-cyclo[8.6.0.0$^{2,7}$.0$^{11,15}$]hexadeca-1(10),2,4,6,8,12,14-heptaene;

16-[4-chloro-3-(trifluoromethyl)phenyl]-4-(2-fluorophenyl)-8,11,13,14,16-pentaazatetracyclo-[8.6.0.0$^{2,7}$.0$^{11,15}$]hexadeca-1(10),2,4,6,8,12,14-heptaene; or N-(5-{16-[4-chloro-3-(trifluoromethyl)phenyl]-8,11,13,14,16-pentaazatetracyclo-[8.6.0.0$^{2,7}$.0$^{11,15}$]hexadeca-1(10),2,4,6,8,12,14-heptaen-4-yl}pyridin-2-yl)acetamide.

12. The compound of claim 1, wherein the compound is selected from:

4-(quinolin-3-yl)-16-[3-(trifluoromethyl)phenyl]-8,11,13,14,16-pentaazatetracyclo-[8.6.0.0$^{2,7}$.0$^{11,15}$]hexadeca-1(10),2,4,6,8,12,14-heptaene;

16-[3,5-bis(trifluoromethyl)phenyl]-4-(quinolin-3-yl)-8,11,13,14,16-pentaazatetracyclo-[8.6.0.0$^{2,7}$.0$^{11,15}$]hexadeca-1(10),2,4,6,8,12,14-heptaene;

16-[3-fluoro-5-(trifluoromethyl)phenyl]-4-(quinolin-3-yl)-8,11,13,14,16-pentaazatetracyclo-[8.6.0.0$^{2,7}$.0$^{11,15}$]hexadeca-1(10),2,4,6,8,12,14-heptaene;

16-[2-fluoro-5-(trifluoromethyl)phenyl]-4-(quinolin-3-yl)-8,11,13,14,16-pentaazatetracyclo-[8.6.0.0$^{2,7}$.0$^{11,15}$]hexadeca-1(10),2,4,6,8,12,14-heptaene;

4-(quinolin-3-yl)-16-[4-(trifluoromethyl)phenyl]-8,11,13,14,16-pentaazatetracyclo-[8.6.0.0$^{2,7}$.0$^{11,15}$]hexadeca-1(10),2,4,6,8,12,14-heptaene; or 2-amino-N-(5-{16-[3-(trifluoromethyl)phenyl]-8,11,13,14,16-pentaazatetracyclo-[8.6.0.0$^{2,7}$.0$^{11,15}$]hexadeca-1(10),2,4,6,8,12,14-heptaen-4-yl}pyridin-2-yl)acetamide.

13. The compound of claim 1, wherein the compound is selected from:

N-(5-{16-[4-chloro-3-(trifluoromethyl)phenyl]-8,11,13,14,16-pentaazatetracyclo[8.6.0.0$^{2,7}$.0$^{11,15}$]-hexadeca-1(10),2,4,6,8,12,14-heptaen-4-yl}pyridin-2-yl)-2-(dimethylamino)acetamide.

N-(5-{16-[4-chloro-3-(trifluoromethyl)phenyl]-8,11,13,14,16-pentaazatetracyclo[8.6.0.0$^{2,7}$.0$^{11,15}$]-hexadeca-1(10),2,4,6,8,12,14-heptaen-4-yl}pyridin-2-yl)-2-(4-methylpiperazin-1-yl)acetamide;

N-(5-{16-[4-chloro-3-(trifluoromethyl)phenyl]-8,11,13,14,16-pentaazatetracyclo[8.6.0.0$^{2,7}$.0$^{11,15}$]-hexadeca-1(10),2,4,6,8,12,14-heptaen-4-yl}pyridin-2-yl)-2-(morpholin-4-yl)acetamide;

N-(5-{16-[4-chloro-3-(trifluoromethyl)phenyl]-8,11,13,14,16-pentaazatetracyclo[8.6.0.0$^{2,7}$.0$^{11,15}$]-hexadeca-1(10),2,4,6,8,12,14-heptaen-4-yl}pyridin-2-yl)-2-(4-oxopiperidin-1-yl)acetamide;

N-(5-{16-[4-chloro-3-(trifluoromethyl)phenyl]-8,11,13,14,16-pentaazatetracyclo[8.6.0.0$^{2,7}$.0$^{11,15}$]-hexadeca-1(10),2,4,6,8,12,14-heptaen-4-yl}pyridin-2-yl)-2-(4-hydroxypiperidin-1-yl)acetamide;

N-(5-{16-[4-chloro-3-(trifluoromethyl)phenyl]-8,11,13,14,16-pentaazatetracyclo[8.6.0.0$^{2,7}$.0$^{11,15}$]-hexadeca-1(10),2,4,6,8,12,14-heptaen-4-yl}pyridin-2-yl)-2-(pyrrolidin-1-yl)acetamide;

5-{16-[4-chloro-3-(trifluoromethyl)phenyl]-8,11,13,14,16-pentaazatetracyclo[8.6.0.0$^{2,7}$.0$^{11,15}$]-hexadeca-1(10),2,4,6,8,12,14-heptaen-4-yl}-N-[2-(pyrrolidin-1-yl)ethyl]pyridin-2-amine;

5-{16-[4-chloro-3-(trifluoromethyl)phenyl]-8,11,13,14,16-pentaazatetracyclo[8.6.0.0$^{2,7}$.0$^{11,15}$]-hexadeca-1(10),2,4,6,8,12,14-heptaen-4-yl}-N-[2-(morpholin-4-yl)ethyl]pyridin-2-amine;

5-{16-[4-chloro-3-(trifluoromethyl)phenyl]-8,11,13,14,16-pentaazatetracyclo[8.6.0.0$^{2,7}$.0$^{11,15}$]-hexadeca-1(10),2,4,6,8,12,14-heptaen-4-yl}-N-(2-methoxyethyl)pyridin-2-amine;

methyl({2-[(5-{16-[3-(trifluoromethyl)phenyl]-8,11,13,14,16-pentaazatetracyclo-[8.6.0.0$^{2,7}$.0$^{11,15}$]hexadeca-1(10),2,4,6,8,12,14-heptaen-4-yl}pyridin-2-yl)amino]ethyl})amine;

dimethyl({2-[(5-{16-[3-(trifluoromethyl)phenyl]-8,11,13,14,16-pentaazatetracyclo-[8.6.0.0$^{2,7}$.0$^{11,15}$]hexadeca-1(10),2,4,6,8,12,14-heptaen-4-yl}pyridin-2-yl)amino]ethyl})amine;

2-(pyrrolidin-1-yl)-N-(5-{16-[3-(trifluoromethyl)phenyl]-8,11,13,14,16-pentaazatetracyclo-[8.6.0.0$^{2,7}$.0$^{11,15}$]hexadeca-1(10),2,4,6,8,12,14-heptaen-4-yl}pyridin-2yl)acetamide;

N-[2-(pyrrolidin-1-yl)ethyl]-5-{16-[3-(trifluoromethyl)phenyl]-8,11,13,14,16pentaazatetracyclo-[8.6.0.0$^{2,7}$.0$^{11,15}$]hexadeca-1(10),2,4,6,8,12,14-heptaen-4-yl}pyridin-2-amine;

2-[(5-{16-[3-(trifluoromethyl)phenyl]-8,11,13,14,16-pentaazatetracyclo[8.6.0.0$^{2,7}$.0$^{11,15}$]-hexadeca-1(10),2,4,6,8,12,14-heptaen-4-yl}pyridin-2-yl)amino]ethan-1-ol;

N-(2-methoxyethyl)-5-{16-[3-(trifluoromethyl)phenyl]-8,11,13,14,16-pentaazatetracyclo-[8.6.0.0$^{2,7}$.0$^{11,15}$]hexadeca-1(10),2,4,6,8,12,14-heptaen-4-yl}pyridin-2-amine;

{2-[(5-{16-[4-chloro-3-(trifluoromethyl)phenyl]-8,11,13,14,16-pentaazatetracyclo-[8.6.0.0$^{2,7}$.0$^{11,15}$]hexadeca-1(10),2,4,6,8,12,14-heptaen-4-yl}pyridin-2-yl)amino]ethyl}-dimethylamine;

5-{16-[4-chloro-3-(trifluoromethyl)phenyl]-8,11,13,14,16-pentaazatetracyclo-[8.6.0.0$^{2,7}$.0$^{11,15}$]-hexadeca-1(10),2,4,6,8,12,14-heptaen-4-yl}-N-[2-(4-methylpiperazin-1-yl)ethyl]-pyridin-2-amine;

2-[(5-{16-[4-chloro-3-(trifluoromethyl)phenyl]-8,11,13,14,16-pentaazatetracyclo-[8.6.0.0$^{2,7}$.0$^{11,15}$]-hexadeca-1(10),2,4,6,8,12,14-heptaen-4-yl}pyridin-2-yl)amino]ethanol; or 4-(pyridin-3-yl)-16-[3-(trifluoromethyl)phenyl]-8,11,14,16-tetraazatetracyclo-[8.6.0.0$^{2,7}$.0$^{11,15}$]-hexadeca-1(10),2,4,6,8,12,14-heptaene.

14. The compound of claim 7, wherein

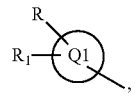

$R_2$, and $R_3$ are as in any one of compounds a, b, c, d, e, f, g, or h of Table A.

15. The compound of claim 7, wherein
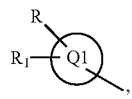
$R_2$, and $R_3$ are as defined as in any of compounds i, j, k, l, m, n, o, p, q, r, s, t, or u in Table A.
16. The compound of claim 7, wherein
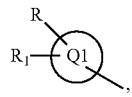
$R_2$, and $R_3$ are as defined as in any of compounds y, z, aa, bb, cc, dd, ee, ff, gg, hh, ii, jj, kk, ll, mm, nn, oo, pp, or qq, in Table A.
* * * * *